(12) United States Patent
Rudy et al.

(10) Patent No.: US 9,259,166 B2
(45) Date of Patent: Feb. 16, 2016

(54) SYSTEMS AND METHODS FOR ON-SITE AND REAL-TIME ELECTROCARDIOGRAPHIC IMAGING (ECGI)

(75) Inventors: Yoram Rudy, St. Louis, MO (US); Yong Wang, Manchester, MO (US)

(73) Assignee: Washington University in St. Louis, St. Louis, MO (US)

( * ) Notice: Subject to any disclaimer, the term of this patent is extended or adjusted under 35 U.S.C. 154(b) by 969 days.

(21) Appl. No.: 13/058,520

(22) PCT Filed: Aug. 10, 2009

(86) PCT No.: PCT/US2009/053262
§ 371 (c)(1),
(2), (4) Date: Apr. 15, 2011

(87) PCT Pub. No.: WO2010/019494
PCT Pub. Date: Feb. 18, 2010

(65) Prior Publication Data
US 2011/0190649 A1    Aug. 4, 2011

Related U.S. Application Data

(60) Provisional application No. 61/087,875, filed on Aug. 11, 2008.

(51) Int. Cl.
*A61B 5/0408* (2006.01)
*A61B 5/00* (2006.01)
(Continued)

(52) U.S. Cl.
CPC ............ *A61B 5/04085* (2013.01); *A61B 5/6805* (2013.01); *A61B 6/503* (2013.01); *A61B 6/5247* (2013.01); *A61B 8/0883* (2013.01); *A61B 8/5261* (2013.01); *A61B 2018/00839* (2013.01)

(58) Field of Classification Search
CPC .. A61B 5/04085; A61B 5/6805; A61B 6/503; A61B 2018/00839; A61B 8/0883; A61B 8/5261; A61B 6/5247
USPC ........................................................ 600/509
See application file for complete search history.

(56) References Cited

U.S. PATENT DOCUMENTS 5,146,926 A    9/1992  Cohen
5,483,968 A    1/1996  Adam et al.

(Continued)

FOREIGN PATENT DOCUMENTS

WO    2007013994    2/2007

OTHER PUBLICATIONS

He et al., "Noninvasive Imaging of Cardiac Transmembrane Potentials Within Three-Dimensional Myocardium by Means of a Realistic Geometry Anisotropic Heart Model"; IEEE Transactions on Biomedical Engineering; 2003; pp. 1190-1202; vol. 50; No. 10.

(Continued)

*Primary Examiner* — Mark W Bockelman
(74) *Attorney, Agent, or Firm* — Tarolli, Sundheim, Covell & Tummino LLP

(57) ABSTRACT

A computer-implemented method for electrocardiographic imaging (ECGI) is provided. The method includes computing a transfer matrix, measuring a plurality of electrical potentials, and computing an estimation of electrical potentials on a surface of interest based at least in part on the measured potentials and the computed transfer matrix. The transfer matrix computing step is performed prior to the measuring step.

17 Claims, 20 Drawing Sheets

(51) Int. Cl.
  *A61B 6/00* (2006.01)
  *A61B 8/08* (2006.01)
  *A61B 18/00* (2006.01)

(56) References Cited

U.S. PATENT DOCUMENTS

| | | | |
|---|---|---|---|
| 6,047,206 | A | 4/2000 | Albrecht et al. |
| 6,772,004 | B2 | 8/2004 | Rudy et al. |
| 6,839,588 | B1 | 1/2005 | Rudy et al. |
| 6,856,830 | B2 | 2/2005 | He |
| 6,975,900 | B2 | 12/2005 | Rudy et al. |
| 7,016,719 | B2 | 3/2006 | Rudy et al. |
| 2002/0128565 | A1 | 9/2002 | Rudy |
| 2005/0197587 | A1 | 9/2005 | Rudy et al. |

OTHER PUBLICATIONS

Sapp et al., "Inverse Solution Electrocardiographic Mapping of Epicardial Pacing Correlates with Three-Dimensional Electroanatomic Mapping"; Computers in Cardiology; 2007; pp. 769-772; vol. 34.

European Search Report for EP0807119 dated Dec. 14, 2012; 8 pages.

Wang et al., Focal atrial tachycardia after pulmonary vein isolation: Noninvasive mapping with electrocardiographic imaging (ECGI), Heart Rhythm, 2007, pp. 1081-1084, vol. 4, No. 8.

Ghanem et al., "Noninvasive Electrocardiographic Imaging (ECGI): Comparison to Intraoperative Mapping in Patients", Heart Rhythm Journal, 2005, pp. 339-354, vol. 2.

Intini et al., "Electrocardiographic imaging (ECGI) a novel diagnostic modality used for mapping of focal left ventricular tachycardia in a young athlete", Heart Rhythm, 2005, pp. 1250-1252, vol. 2.

Jia et al., "Electrocardiographic imaging of cardiac resynchronization therapy in heart failure: Observation of variable electrophysiologic responses", Heart Rhythm, 2006, pp. 296-310, vol. 3.

Ramanathan et al., "Noninvasive Imaging for Cardiac Electrophysiology and Arrhythmia", Nature Medicine, 2004, 7 pages.

Ramanathan et al., "Activation and repolarization of the normal human heart under complete physiological conditions", Proc. Natl. Acad. Sci., U.S.A. (PNAS), 2006, pp. 6309-6314, vol. 103.

Beyond the EKG, to a Hypersensitive heart monitor., New York Times, Apr. 22, 2004.

Wang et al., "Noninvasive Electrocardiographic Imaging (ECGI) of Scar-Related Atypical Flutter" Heart Rhythm, 2007, pp. 1565-1567.

FIG. 5C $$\text{Matrix } V_{SM} = \begin{bmatrix} 1 & 0 & 0 & 0 \\ 0 & 1 & 0 & 0 \\ 0 & 0 & 1 & 0 \\ 0 & 0 & 0 & 1 \end{bmatrix}$$

$$V_{SMBE1} = \begin{bmatrix} 1 \\ 0 \\ 0 \\ 0 \end{bmatrix} \quad V_{SMBE2} = \begin{bmatrix} 0 \\ 1 \\ 0 \\ 0 \end{bmatrix} \quad V_{SMBE3} = \begin{bmatrix} 0 \\ 0 \\ 1 \\ 0 \end{bmatrix} \quad V_{SMBE4} = \begin{bmatrix} 0 \\ 0 \\ 0 \\ 1 \end{bmatrix}$$

The NxN matrix $V_{SM}$ is decomposed into N basis element vectors $V_{SMBE1}$-$V_{SMBEn}$ as shown (N is 4 in this example). it thus follows that:

$$V_M = \begin{bmatrix} V_M(1) \\ V_M(2) \\ V_M(3) \\ V_M(4) \end{bmatrix} = V_M(1)*V_{SMBE1} + V_M(2)*V_{SMBE2} + V_M(3)*V_{SMBE3} + V_M(4)*V_{SMBE4} = V_{SM}*V_M$$

FIG. 5D

Computing $V_{SSi}$ = Reg (A, $V_{SMBEi}$) for i=1 through N will yield N
simulated solution vectors $V_{SSi}$ (in this example, N is 4 and P is 6):

$$V_{SS1} = \begin{bmatrix} V_{SS1}(1) \\ V_{SS1}(2) \\ V_{SS1}(3) \\ V_{SS1}(4) \\ V_{SS1}(5) \\ V_{SS1}(6) \end{bmatrix} \quad V_{SS2} = \begin{bmatrix} V_{SS2}(1) \\ V_{SS2}(2) \\ V_{SS2}(3) \\ V_{SS2}(4) \\ V_{SS2}(5) \\ V_{SS2}(6) \end{bmatrix} \quad V_{SS3} = \begin{bmatrix} V_{SS3}(1) \\ V_{SS3}(2) \\ V_{SS3}(3) \\ V_{SS3}(4) \\ V_{SS3}(5) \\ V_{SS3}(6) \end{bmatrix} \quad V_{SS4} = \begin{bmatrix} V_{SS4}(1) \\ V_{SS4}(2) \\ V_{SS4}(3) \\ V_{SS4}(4) \\ V_{SS4}(5) \\ V_{SS4}(6) \end{bmatrix}$$

$$\text{Matrix C} = \begin{bmatrix} V_{SS1}(1) & V_{SS2}(1) & V_{SS3}(1) & V_{SS4}(1) \\ V_{SS1}(2) & V_{SS2}(2) & V_{SS3}(2) & V_{SS4}(2) \\ V_{SS1}(3) & V_{SS2}(3) & V_{SS3}(3) & V_{SS4}(3) \\ V_{SS1}(4) & V_{SS2}(4) & V_{SS3}(4) & V_{SS4}(4) \\ V_{SS1}(5) & V_{SS2}(5) & V_{SS3}(5) & V_{SS4}(5) \\ V_{SS1}(6) & V_{SS2}(6) & V_{SS3}(6) & V_{SS4}(6) \end{bmatrix}$$

The simulated solution vectors $V_{SSi}$ are recomposed to form PxN matrix C

The estimates of the cardiac surface potentials can
then be computed as:
$$V_S = C * V_M$$

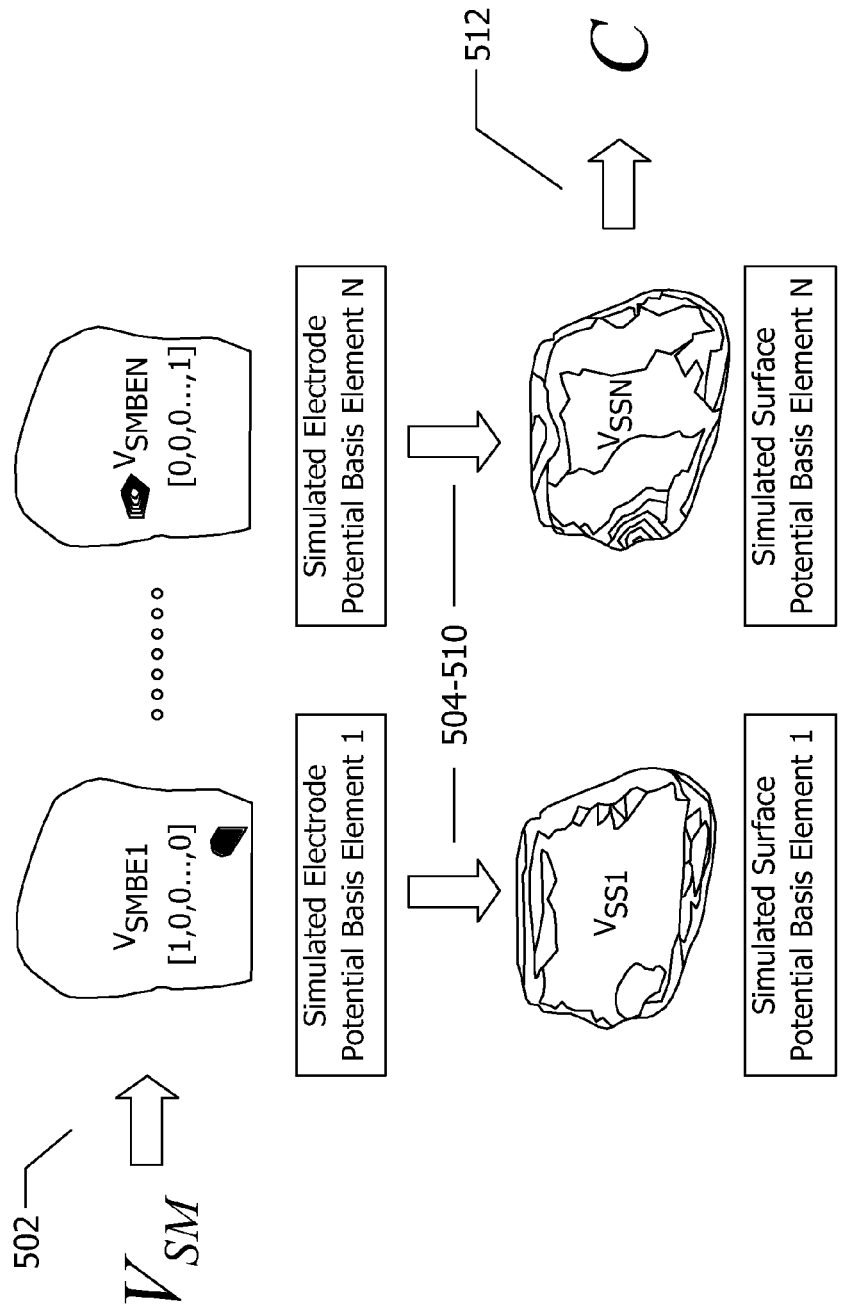

SYSTEMS AND METHODS FOR ON-SITE AND REAL-TIME ELECTROCARDIOGRAPHIC IMAGING (ECGI)

CROSS-REFERENCE TO RELATED APPLICATIONS

This application is a 35 U.S.C. §371 national stage application of PCT/US2009/053262, filed Aug. 10, 2009, which claims priority to U.S. Provisional Application No. 61/087,875, Aug. 11, 2008, the entireties of which are hereby incorporated by reference for all purposes.

STATEMENT REGARDING FEDERALLY SPONSORED RESEARCH OR DEVELOPMENT

This invention was made with government support under NIH-NHLBI Grant R37-HL-33343 awarded by the National Institutes of Health (NIH). The government may have certain rights in the invention.

FIELD OF THE INVENTION

This disclosure relates to improved techniques for estimating electrical conditions such as electrical potentials on a surface of interest, particularly in connection with electrocardiographic imaging (ECGI). For example, embodiments of the present disclosure relate to ECGI techniques that reduce the processing time required to compute estimations of cardiac electrical potentials after acquisition of body surface potentials.

BACKGROUND

Previous works by the inventors herein in the field of ECGI are represented by U.S. Pat. No. 6,772,004, entitled "System and Method for Non-Invasive Electrocardiographic Imaging", U.S. Pat. No. 7,016,719, entitled "System and Methods for Noninvasive Electrocardiographic Imaging (ECGI) Using Generalized Minimum Residual (GMRES)", U.S. Pat. No. 6,975,900, entitled "Systems and Methods for Determining a Surface Geometry", U.S. Pat. No. 6,839,588, entitled "Electrophysiological Cardiac Mapping System Based on a Non-Contact Non-Expandable Miniature Multi-Electrode Catheter and Method Therefor", U.S. Patent Application Publication 2005/0197587, entitled "Determining a Surface Geometry of an Object", and PCT publication WO 2007/013994, entitled "System and Method for Noninvasive Electrocardiographic Image (ECGD", the entire disclosures of all of which are incorporated herein by reference.

These works disclose the computation of cardiac surface potentials, electrograms, and isochrones from measured electrode potentials using various techniques. The techniques described herein can be used in conjunction with various combinations of techniques described in the above-referenced works, as will be apparent to those of ordinary skill in the art.

SUMMARY

Embodiments described herein facilitate improving the speed of cardiac surface electrical potential estimations such that those estimations (and, optionally, images derived therefrom) can be made available "on-site" during a medical procedure. When ECGI is said to be practiced "on-site", this means that the estimations of cardiac surface electrical potentials are produced contemporaneously with a medical procedure during which the electrode data for those images is measured. For example, with a medical procedure that is performed in a cardiac electrophysiology (EP) laboratory, such as catheter ablation of the arrythmia substrate, on-site ECGI allows for heart electrical potentials to be estimated on-site in the EP lab while the catheter ablation is ongoing. With such on-site feedback, ECGI can be used to guide the procedure and evaluate its results. The "on-site" description does not necessarily require that an ECGI image or electrical potential estimation be generated and displayed in the same room in which the medical procedure is occurring, although this is facilitated.

BRIEF DESCRIPTION OF THE DRAWINGS

FIGS. 5A-5D depicts an exemplary process flow for computing transfer matrix C in accordance with the embodiments of FIGS. 4A and 4B;

FIGS. 6A and 6B provide graphical illustrations corresponding to the computation of transfer matrix C and the computation of estimated surface potentials based on C and measured potentials;

DETAILED DESCRIPTION

Techniques are described herein to facilitate improving the latency between data acquisition and estimating the electrical potentials on a surface of interest (as well as image generation corresponding to such estimated electrical potentials). The term "surface of interest" as used herein refers to any surface to which the inventive techniques described herein can be applied. In exemplary embodiments, the surface of interest is a cardiac surface for ECGI. In two exemplary embodiments, the surface of interest is the epicardial cardiac surface and endocardial cardiac surface, respectively. However, it should be noted that the techniques described herein may be adapted to work with other surfaces, and are not limited to cardiac surfaces.

Embodiments described herein facilitate production of ECGI data and images such that ECGI data and images can be made available within a few minutes (or considerably less) of acquiring electrode potential data. This means that ECGI images produced from electrode potential data measured during a medical procedure can be made available on-site during that medical procedure. This allows ECGI images to be used interactively by medical personnel during the medical procedure. Such ECGI images can be especially useful to medical personnel with respect to guiding a medical procedure, as well as evaluating the results of that medical procedure.

Some embodiments disclose a real-time technique wherein ECGI data and images can be produced during a medical procedure within milliseconds after acquiring electrode potential data. Each frame of ECGI data can be computed from a frame of measured electrode potentials in less than 1 millisecond. In an exemplary embodiment wherein the sampling rate of acquiring frames of measured electrode potentials is 1 kHz, it should be readily understood that such computational speed means that ECGI frames can be generated in real-time. This powerful embodiment essentially facilitates "live" views of the estimated electrical potentials on the surface of interest. In doing so, according to an exemplary embodiment, the inventors have devised a technique for pre-computing a transfer matrix which allows for the computation of estimated potentials on the surface of interest from the measured potentials via direct matrix multiplication.

In another exemplary embodiment, the system employs a multi-processing computer architecture to further improve the performance of ECGI.

It should be noted that the term "medical procedure" as used herein refers to any medical procedure without limitation. While reference is made herein to specific procedures (e.g. catheter ablation), such references should not be construed as limiting.

Figure 1:
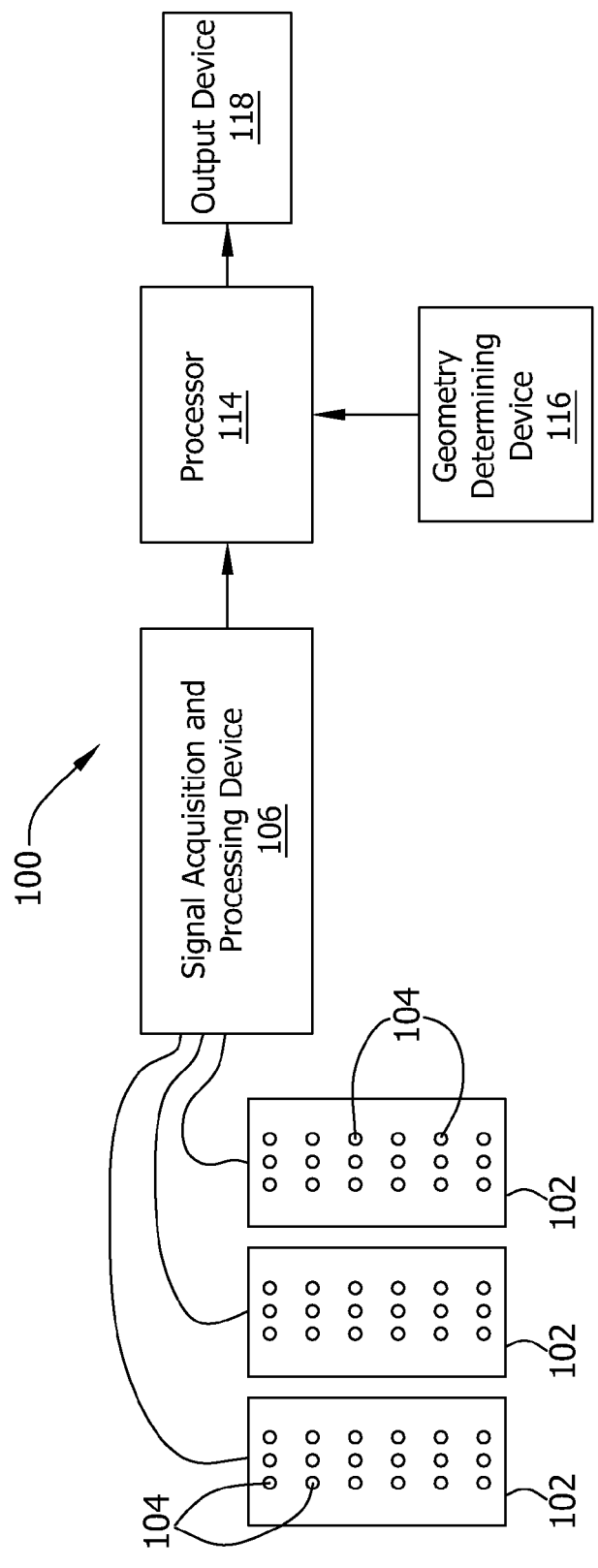
FIG. 1 illustrates a block diagram overview of an exemplary system for non-invasive ECGI.

FIG. 1 depicts a block diagram overview of an exemplary system 100 for performing non-invasive ECGI. The system 100 comprises a plurality of electrodes 104 (mounted on strips 102, a vest, or in some other array) in communication with a signal acquisition and processing device 106. The electrodes 104 serve to sense a plurality of electrical potentials on a patient's body surface. The signal acquisition and processing device 106 operates to process this sensed data to a form suitable for digital processing, as is known in the art. The system 100 also comprises a geometry determining device 116 that serves to generate data that is indicative of the geometrical relationship between the electrodes 104 and one or more points of interest within the patient (e.g., the patient's epicardial cardiac surface).

Processor 114 operates to (1) receive data from both the electrodes 104 (by way of the signal acquisition and processing device 106) and the geometry determining device 116 and (2) reconstruct epicardial cardiac surface potentials from the received data. The reconstructed epicardial potentials can then be used to provide, via the output device 118, images such as electrograms, isochrones (activation maps), epicardial cardiac potential maps, or other data representations derived from the epicardial potentials (e.g., integral maps, recovery maps, activation-recovery interval maps, etc.). An example of a suitable processor 114 is a conventional desktop or laptop computer, such as a 2.4 GHz laptop computer with a gigabyte of RAM. However, as would be understood by those having ordinary skill in the art, any processor with sufficient memory resources and computational speed would be suitable for use as processor 114. Furthermore, as explained in greater detail herein, by using a multi-processor or multi-core processor as processor 114, significant improvements can be made in computational latency.

Output device 118 may be any device capable of effectively communicating the results of the reconstruction to a user, such as a display monitor and/or printer associated with the processor 114, as would be understood by those having ordinary skill in the art.

It is also worth noting that a variety of known techniques for electronic data communication can be used as the data links between the various elements depicted in FIG. 1, as would be understood by those of ordinary skill in the art. Furthermore, it should be understood that the ECGI techniques described herein can readily be implemented in software and/or hardware for execution by one or more processors to compute epicardial cardiac surface potentials. Moreover, in some instances the processor 114 and geometry determining device may be integrated into the same platform, such as a CT scanner, an MRI scanner, a bi-plane X-ray fluoroscopy apparatus, or an ultrasound echocardiography apparatus that has ECGI processing capabilities built-in.

Electrodes 104 may be arranged on a plurality of strips 102 that can be placed in position on the torso of a patient undergoing ECGI. Alternatively, a vest arrangement as shown in U.S. Pat. Nos. 6,772,004 and 7,016,719 may also be used. As mentioned above, electrodes 104 measure the electrical potentials on the patient's torso. The electrodes 104 that are used are, in some embodiments, electrodes that are visible in the imaging modality used by the geometry determining device 116. Otherwise, appropriate markers may be placed on the electrodes to render them visible in the images produced by the geometry determining device 116. When practicing ECGI, the total number of electrodes 104, the number of electrodes 104 per strip 102, the number of electrode strips 102, and the placement of the electrode strips 102 on the patient can be variable according to the needs of the ECGI practitioner. In an exemplary embodiment, as much of the patient's torso (front, back, and sides) as possible is covered by electrodes 104. For example, the total number N of electrodes 104 could range from 120 to 250. However, the value of N may be more or less than a value within this range, as would be understood by a person having ordinary skill in the art. However, the inventors herein believe that the use of too few electrodes will reduce the accuracy of the reconstructed epicardial cardiac surface potentials.

The electrodes can be wet electrodes or dry electrodes, as would be understood by those having ordinary skill in the art. By avoiding the use of gels, short circuiting risks arising from a high concentration of electrodes can be reduced. An example of a suitable type of electrode to obtain body surface potentials is a silver/silver chloride (Ag/AgCl) electrode. However, other types of electrodes such as carbon electrodes can also be used. If CT is used as the imaging modality for the geometry determining device, CT markers may be disposed on the carbon electrodes to render them visible in the CT images.

In an exemplary embodiment, the signal acquisition and processing device 106 is a multi-channel device that operates to receive the sensed electrical potentials from the electrodes 104, process that data, and supply it to processor 114. Practitioners may select a commercially-available system to use as the signal acquisition and processing device 106. For example, the Active Two system that is available from Bio-Semi of WG-Plein 129, 10545C, Amsterdam, Netherlands, which is a 256-channel, DC amplifier, 24 bit resolution biopotential measurement system, may serve as device 106. The Active Two biopotential measurement system includes an analog-to-digital converter (ADC) that receives electrode data from electrodes 104, a power source (battery and charger), a USB2 receiver that receives the digital output from the ADC via a fiber optic connection and provides the digital electrode data to acquisition software resident on processor 114 via a USB2 connection. The analog input box that is also part of the Active Two system may be omitted from the practice of the exemplary embodiment.

It should also be noted that custom-designed signal acquisition and processing device 106 can also be used, such as the one described in U.S. Pat. Nos. 6,772,004 and 7,016,719.

Figure 2A:
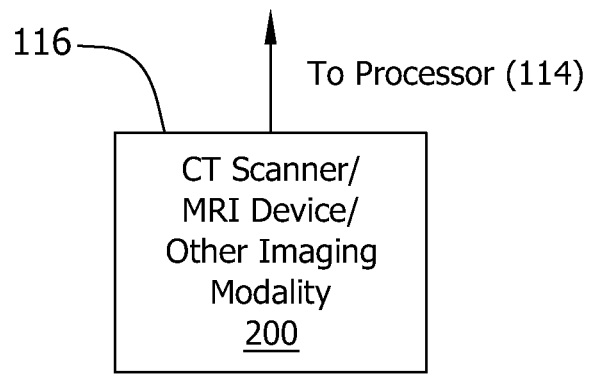
FIGS. 2A and 2B depict exemplary geometry determining devices.

The geometry determining device 116 may take a variety of forms, as described in U.S. Pat. Nos. 6,772,004, 6,975,900, and 7,016,719, including x-ray, ultrasound, computed tomography (CT) and magnetic resonance imaging (MRI). For example, as shown in FIG. 2A, the geometry determining device 116 may take the form of a CT scanner or MRI device 200. The operation and collection of data therefrom will be apparent to those of ordinary skill in the art. In one embodiment, the CT scanner/MRI device 200 is used to generate data, or images, to determine torso geometry and, consequently, body surface electrode positions as well as an epicardial envelope surrounding the heart. As those of skill in the art will appreciate, the epicardial envelope is a suitable estimate of the epicardial cardiac surface itself, which could also be determined. The term "epicardial envelope" as used herein refers to any surface on or outside the epicardial cardiac surface and inside the volume defined by the body surface that at least partially encloses the epicardial cardiac surface. While the term "epicardial envelope" encompasses the actual outer surface of the epicardium, the term "epicardial cardiac surface" as used herein refers specifically to the actual outer surface of the epicardium.

Figure 2B:
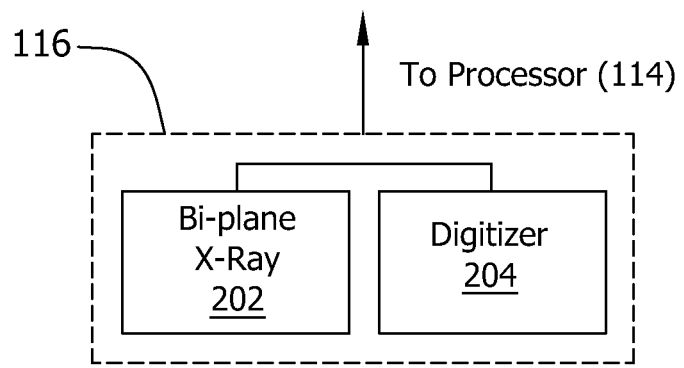

It should also be recognized that locating the epicardial envelope or surface necessarily involves location of the heart. As a further example, as shown in FIG. 2B and described in greater detail in U.S. Pat. Nos. 6,772,004, 6,975,900, and 7,016,719, the geometry determining device 116 may also take the form of a bi-plane x-ray machine 202 and a digitizer 204, although other imaging modalities (e.g., ultrasound) could also be used.

While FIG. 1 depicts a non-invasive ECGI system, it should also be understood that ECGI can be practiced using invasive techniques. For example, U.S. Pat. No. 6,839,588 describes an invasive ECGI technique wherein an electrode catheter is inserted into a patient and positioned near the patient's endocardium to sense data relating to endocardial electrical potentials. Such a catheter may include a plurality of electrodes. As noted below, embodiments of the present disclosure can employ non-invasive or invasive techniques for measuring the electrical potentials from which the cardiac surface electrical potentials are estimated.

Figure 3A:
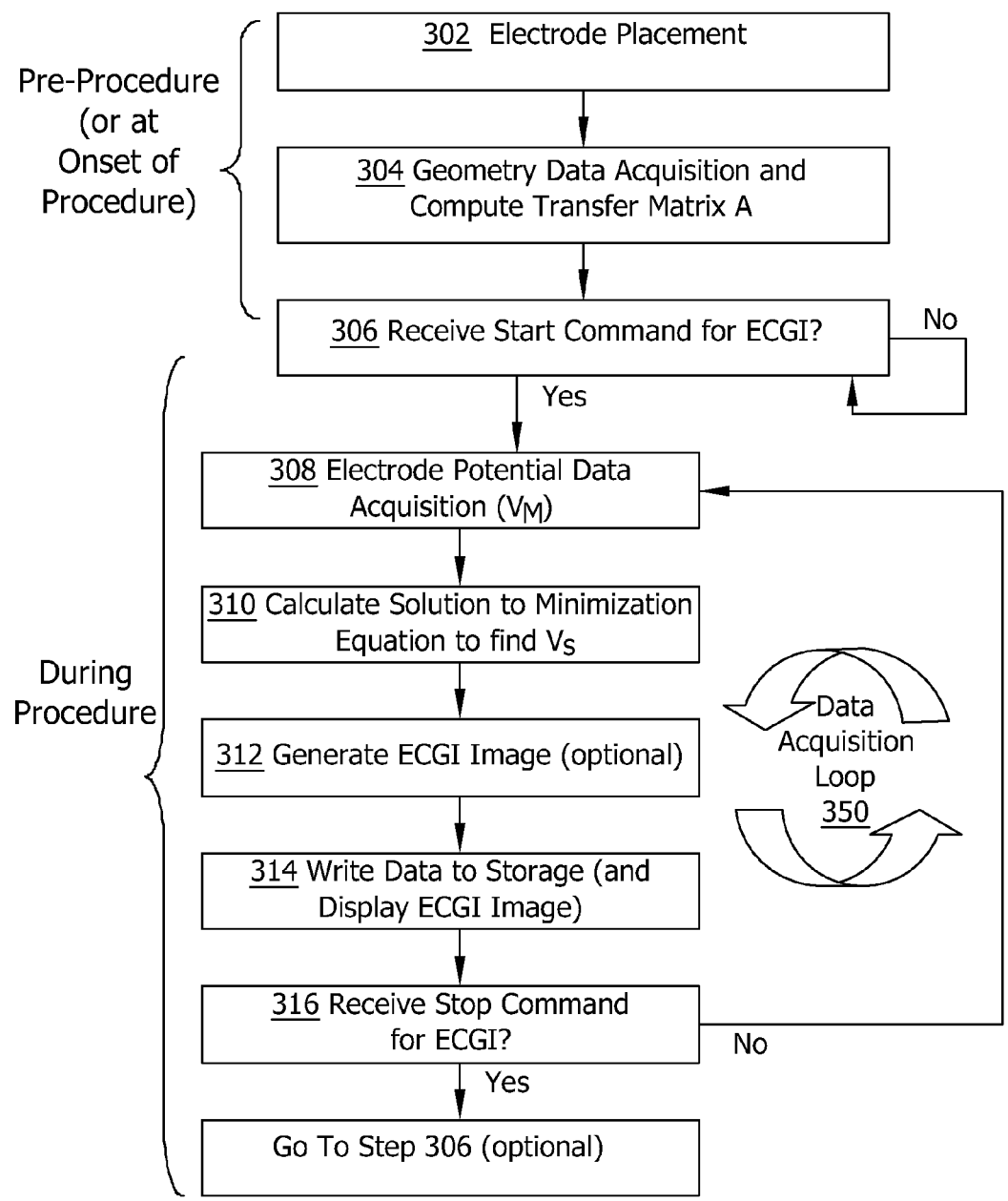
FIGS. 3A-3B illustrate a flowchart of an exemplary embodiment for practicing on-site ECGI.

On-Site ECGI:

FIG. 3A illustrates an exemplary process flow for practicing on-site ECGI. As noted above, when ECGI is said to be practiced "on-site", this means that the cardiac surface electrical potential estimations are produced contemporaneously with a medical procedure during which the electrode data for those estimations is measured.

At step 302, the practitioner places electrodes for sensing the patient's electrical potentials. Step 302 is, in some embodiments, performed prior to the medical procedure or at the outset of the medical procedure. The practitioner can choose to place electrodes invasively or non-invasively. An invasive technique is typically used when the surface of interest is the endocardium, but this is not necessarily the case. As noted above, an exemplary invasive electrode sensing technique suitable for use in connection with exemplary embodiments of the present disclosure is described in U.S. Pat. No. 6,839,588. A non-invasive technique is typically used when the surface of interest is the epicardium, but this is not necessarily the case. As noted above, an exemplary non-invasive electrode sensing technique suitable for use in connection with exemplary embodiments of the present disclosure is described in U.S. Pat. Nos. 6,772,004, 6,975,900, and 7,016, 719, PCT Publication WO 2007/013994, and U.S. Patent Application Publication 2005/0197587. It should also be noted that a practitioner may optionally employ both invasive and non-invasive electrode sensing techniques simultaneously.

At step 304, geometry data is acquired using a geometry determining device such as a CT scanner. In some embodiments, this geometry data defines spatial relationships between the electrodes and various torso features (including cardiac features such as heart position and heart surface locations). In an exemplary embodiment wherein the surface of interest is the endocardium, the geometry data is acquired as described in U.S. Pat. No. 6,839,588. In an exemplary embodiment wherein the surface of interest is the epicardium, the geometry data is acquired as described in U.S. Pat. Nos. 6,772,004, 6,975,900, and 7,016,719, PCT Publication WO 2007/013994, and U.S. Patent Application Publication 2005/0197587. It should also be noted that step 304 may not be necessary if the geometry data is already known.

Step 304 is performed before beginning electrode data acquisition, and optionally prior to the medical procedure or at the outset of the medical procedure. As part of this acquisition, computer algorithms for automated or semi-automated image segmentation and labeling may be used to define the geometrical data (for example a semi-automatic active contour method). However, contouring/segmentation could optionally be performed manually.

Further at step 304, a transfer matrix A that translates the measured electrode potentials to electric potentials on the surface of interest is computed. Thus, the matrix A is optionally available to the computing system at the start of electrode potential data acquisition (or shortly thereafter). As explained in U.S. Pat. Nos. 6,772,004, 6,975,900, and 7,016,719, PCT Publication WO 2007/013994, and U.S. Patent Application Publication 2005/0197587, the values of transfer matrix A are defined by the geometry data acquired at step 304. The relationship between the transfer matrix A, the measured electrode potentials $V_M$ and the surface of interest electric potentials $V_S$ can be expressed as:

$$V_M = AV_S \quad (1)$$

wherein $V_M$ is an N×1 vector, wherein $V_S$ is a P×1 vector, wherein N represents the number of electrodes used to sense electrical potentials, and wherein P represents the number of locations on the surface of interest for which the electrical potentials are estimated. It should be noted that P need not be the same value as N. It should also be noted that in a non-invasive embodiment wherein the electrode measurements are made from a patient's torso surface, $V_M$ can be expressed as $V_T$. It should further be noted that in embodiments wherein the surface of interest is the epicardial surface or endocardial surface, $V_S$ can be expressed as $V_E$.

At step 306 the system waits to receive a start command from the system operator. When the system receives a start command, flow proceeds to step 308.

At step 308, electrode potential data is measured and recorded in data storage such as computer memory. Step 308 is performed during the medical procedure. In some embodiments, potential data is measured and recorded from all of the electrodes during step 308. This combined electrode potential data, acquired in one execution of step 308, is referred to herein as one "frame" of electrode potential data (represented as the vector $V_M$ in Equation (1) above).

At step 310, the process computes an estimate of the electrical potentials on the surface of interest ($V_S$). Step 310 may be performed during the medical procedure. As noted above, $V_S$ represents an estimate of the electric potentials on the surface of interest at a plurality P of discrete locations on the surface of interest. With reference to Equation (1) above, due to the ill-posed nature of A, direct calculation of $V_S$ cannot be computed as $A^{-1}*V_M$. $V_S$ may therefore be calculated as the vector which minimizes the following energy minimization equation:

$$\min_{V_S}(\|AV_S-V_M\|^2+t\|LV_S\|^2) \quad (2)$$

In Equation (2), t is a regularization parameter and L is an identity or a differential (first or higher order) operator. In some embodiments, t is found using the CRESO (Composite Residual and Smoothing Operator) method, as described in U.S. Pat. No. 6,772,004. A regularization technique is used to solve equation (2), and the regularization technique may take the form of Tikhonov regularization, as described in U.S. Pat. No. 6,772,004. However, it should be noted that a variety of other regularization techniques may be used, such as GMRes regularization. Examples of such regularization schemes are described in U.S. Pat. Nos. 6,772,004, 6,975,900, and 7,016,719, PCT Publication WO 2007/013994, and U.S. Patent Application Publication 2005/0197587. It should be understood that other regularization techniques can also be applied, in addition to, or in lieu of, the techniques mentioned above. Furthermore, in an exemplary embodiment, the regularization calculations may depend on limiting the value of the spatial derivative of electric potential on the surface of interest to a certain threshold value.

For purposes of concise expression, the solution "z" to Equation (2) above will be expressed as:

$$z=\text{Reg}(x,y) \quad (3)$$

wherein the function Reg(x,y) is a shorthand reference for the solving of Equation (2) using input variable "x" as the "A" term in Equation (2) and using input variable "y" as the "$V_M$" term in Equation (2) to find "z" as the "$V_S$" term in Equation (2). Thus, $V_S$ in the on-site embodiment may be computed according to Equation (2) using the shorthand of Equation (3) as:

$$V_S=\text{Reg}(A,V_M) \quad (4)$$

Because the process flow of FIG. 3A operates to compute A prior to measuring electrode potentials at step 308, the embodiment of FIG. 3A is capable of computing $V_S$ in a sufficiently expedited manner as to make $V_S$ available to medical personnel during the same procedure in which $V_M$ was measured.

At step 312, the system can optionally generate an ECGI image, which can be any of the image types discussed above. For example, the ECGI images may take the form of electrograms, isochrones (activation maps), epicardial cardiac potential maps, or other data representations derived from the estimated surface potentials (e.g., integral maps, recovery maps, activation-recovery interval maps, etc.), as described in U.S. Pat. Nos. 6,772,004, 6,975,900, and 7,016,719, PCT Publication WO 2007/013994, and U.S. Patent Application Publication 2005/0197587. Each ECGI image optionally comprises a visual representation of the solution $V_S$ calculated at step 310. The system may be configured to generate an ECGI image at each iteration (i.e. for each frame of data), for a fraction of iterations, or in response to user-input as described below. The system may optionally display the generated image until the next image is generated in a subsequent iteration. For example, the images may be displayed on one or more video monitors available to the medical personnel, wherein the monitors can be Liquid Crystal Displays (LCDs), as an example.

It should also be noted that various flow control mechanisms can be applied to alter the flow of FIG. 3A. For example, at step 312, the process flow can be made interactive according to the requests of a practitioner such as a medical professional conducting the medical procedure. For example, such a request may be made during the medical procedure by medical personnel. Thus, in an exemplary embodiment, step 312 may be optional, and a request for ECGI data such as an ECGI image may be received, and the decision to generate an ECGI image for a given iteration may be made in response to the received request. In a non-limiting exemplary embodiment, the system may be configured such that step 310 is performed on-demand as well, such that surface potential estimates are only calculated in response to a request for an ECGI image.

At step 314, the system writes data to data storage (such as a computer memory), from which it can later be retrieved for additional use. In some embodiments, the data written to memory comprises at least $V_S$, and, optionally, $V_M$, $V_S$, and any generated images. Optionally, this data is stored for later use, for example according to the exemplary embodiment depicted in FIG. 3B. Step 314 may also be performed during the medical procedure. It should be noted that the system may optionally be configured such that a practitioner can toggle data recording on and off independently (i.e. toggle whether step 314 is performed).

It should be noted that steps 308, 310, 312, and 314 may be repeated in a data acquisition loop 350 as illustrated in FIG. 3A. The frequency of looping back to step 308 can be variable according to the preferences of a practitioner. Electrode potential data at step 308 can be acquired from the electrodes at a sampling rate of about 1 kHz, or 1 frame per millisecond (ms). In other words, step 308 can be executed approximately once every millisecond. However, it should be understood that a wide range of frequencies are possible. In an exemplary embodiment, steps 308, 310, 312, and 314 can be executed each time a data measurement is taken from the electrodes. However, it should be noted that some steps could be skipped for some iterations of the data acquisition loop 350. For example, steps 310 and 312 might be performed only in half of the iterations of the data acquisition loop 350. A wide variety of adjustments for the ratio of performance of step 308 relative to steps 310 and 312 can thus be used.

In one embodiment, the data acquisition loop 350 runs continuously during the medical procedure, although this need not be the case. For example, a practitioner might pause the data acquisition loop 350 by issuing a stop command at step 316, and later re-start the data acquisition loop 350 by issuing a start command at step 306.

In some embodiments, steps 302, and 304 are executed only once for a given medical procedure, but it is foreseeable that additional executions may be desirable (particularly in an invasive version of step 302, which may require a device such as an electrode catheter to be re-positioned multiple times throughout the procedure).

Steps 310, 312, and 314 can be executed outside of data acquisition loop 350, for example in a parallel process, although this need not be the case. It should be noted that the system can be configured to perform steps 310, 312, and 314 in parallel with step 308. In some embodiments, step 310 is performed in real-time with respect to step 308. In one embodiment, both steps 310 and 312 are performed in real-time with respect to step 308.

It should also be noted that steps 308 (at least the data acquisition portion of step 308), 310, 312, 314, 316, and 318 are performed by a processor such as processor 114 of FIG. 1.

In an exemplary embodiment, processor 114 can be a single processor having multiple processing cores (e.g., a dual core processor). With such an embodiment, the computational steps of steps 308, 310, 312, and 314 can be distributed across different processing cores to reduce the latency between steps 308 and 310 (as well as step 312 and subsequent operations). For example, steps 308 and 310 can be allocated to different processing cores or steps 308 and 310 can be allocated to one core of the multi-core processor while steps 312 and 314 are allocated to a different core of the multi-core processor. Thus, having acquired the potential data at step 308 and having received a request at step 312 to generate one (or more) ECGI images, the system will be capable of generating the requested images while also continuing to compute estimated surface potentials at step 312 for new data. It should also be noted that rather than using a multi-core processor, multiple processors can be used to the same effect. Moreover, the system may optionally contain multiple computer memories such that the system is capable of writing acquired electrode potential data to one computer memory while simultaneously writing estimated surface potential data to a second memory.

Figure 3B:
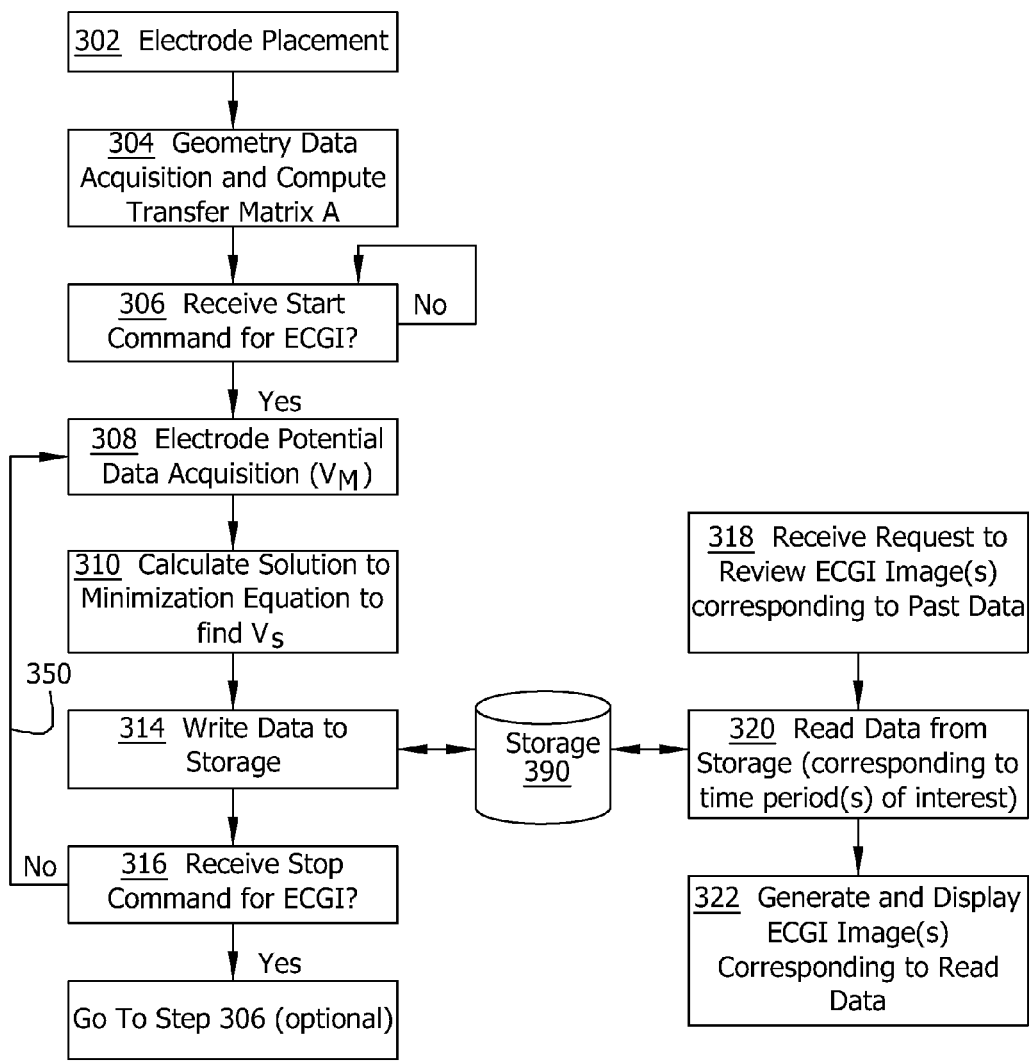

FIG. 3B depicts an exemplary embodiment wherein the system is configured to display ECGI images on demand based on previously recorded $V_S$ data. Steps 318, 320, and 322 are responsible for generating and displaying images corresponding to the previously recorded data. As can be seen in FIG. 3B, images can be generated from previously recorded data while the system simultaneously continues to execute the data acquisition loop.

At step 318, the system receives a request for an ECGI image corresponding to a particular time period. This request may also define an ECGI image type (e.g., electrogram, isochrone, etc.) and a time period of interest for which the ECGI data is desired. The request can be input into the system in a variety of ways. For example, a doctor could be interested in a particular cardiac cycle, and the doctor would thus request to see an ECGI image sequence corresponding to that particular cardiac cycle.

At step 320, the system reads $V_S$ data from storage 390 corresponding to the time period(s) of interest.

At step 322, the system generates and displays the appropriate ECGI image(s) corresponding to the retrieved $V_S$ data. The ECGI image(s) displayed at step 322 are optionally displayed during a medical procedure, and may correspond to data recorded previously during the same medical procedure. However, it is foreseeable that a practitioner may wish to display ECGI images corresponding to a different time period (e.g. a prior medical procedure). In some embodiments, the system is capable of displaying multiple ECGI images simultaneously (e.g. on multiple monitors), and in an exemplary embodiment could display images corresponding to data recorded during the current medical procedure concurrently with ECGI images corresponding to data recorded during a prior medical procedure. Furthermore, the system may optionally be configured to simultaneously display a "current" view of ECGI data (e.g. images generated at step 312) as well as images corresponding to previously recorded data (e.g. images generated at step 322).

It should be noted that the process flow of FIG. 3B may optionally include step 312 within loop 350 between steps 310 and 314. In this way, the data written to memory at step 314 can also include the ECGI image(s) generated at step 312. Thus, when step 320 operates to retrieve data from memory, step 320 can be configured to retrieve the appropriate ECGI image(s) that were previously generated at step 312. In such a scenario, step 322 need not necessarily include an image generation feature. Further still, it should be noted that the system can be configured to display ECGI images corresponding to pre-recorded data concurrently with "live" ECGI images, In such a scenario, step 322 would operate to display both the currently-generated ECGI image from step 312 and a previously-recorded ECGI image from a previous iteration of step 312 or from a retrieval and generation operation at steps 320 and 322.

Further still, for the embodiments of FIGS. 3A and 3B, it should be noted that step 310 may optionally be removed from loop 350 and placed into the process flow following step 320 (or in some other location allowing for on-demand performance of step 310). In such an instance with respect to FIG. 3B, step 314 would operate to write $V_M$ data to memory 390, and step 320 would operate to retrieve the appropriate frame(s) of $V_M$ data from memory which corresponding to the time period(s) of interest. Following this retrieval, step 310 would operate to compute $V_S$, and step 322 would operate to generate the appropriate ECGI image(s). In this way, the computation of specific $V_S$ frames can also be performed in an on-demand manner.

Thus, with respect to the exemplary process flows of FIGS. 3A and 3B, by computing A prior to acquiring $V_M$, practitioners can expedite the computation of $V_S$, thereby allowing ECGI to be practiced on-site during medical procedures.

Figure 4A:
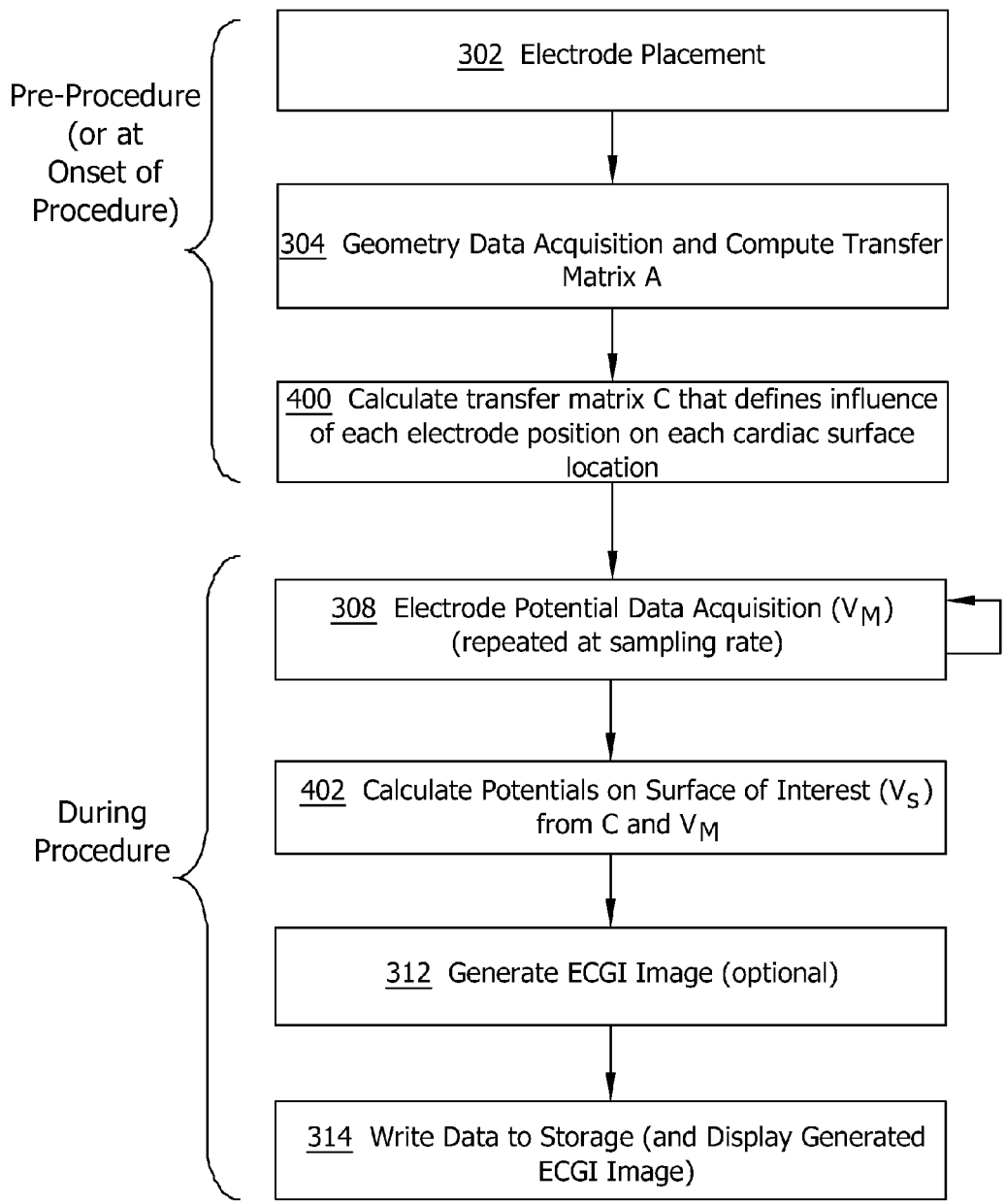
FIGS. 4A-4B illustrate a flowchart of an exemplary embodiment for practicing real-time ECGI.
Figure 4B:
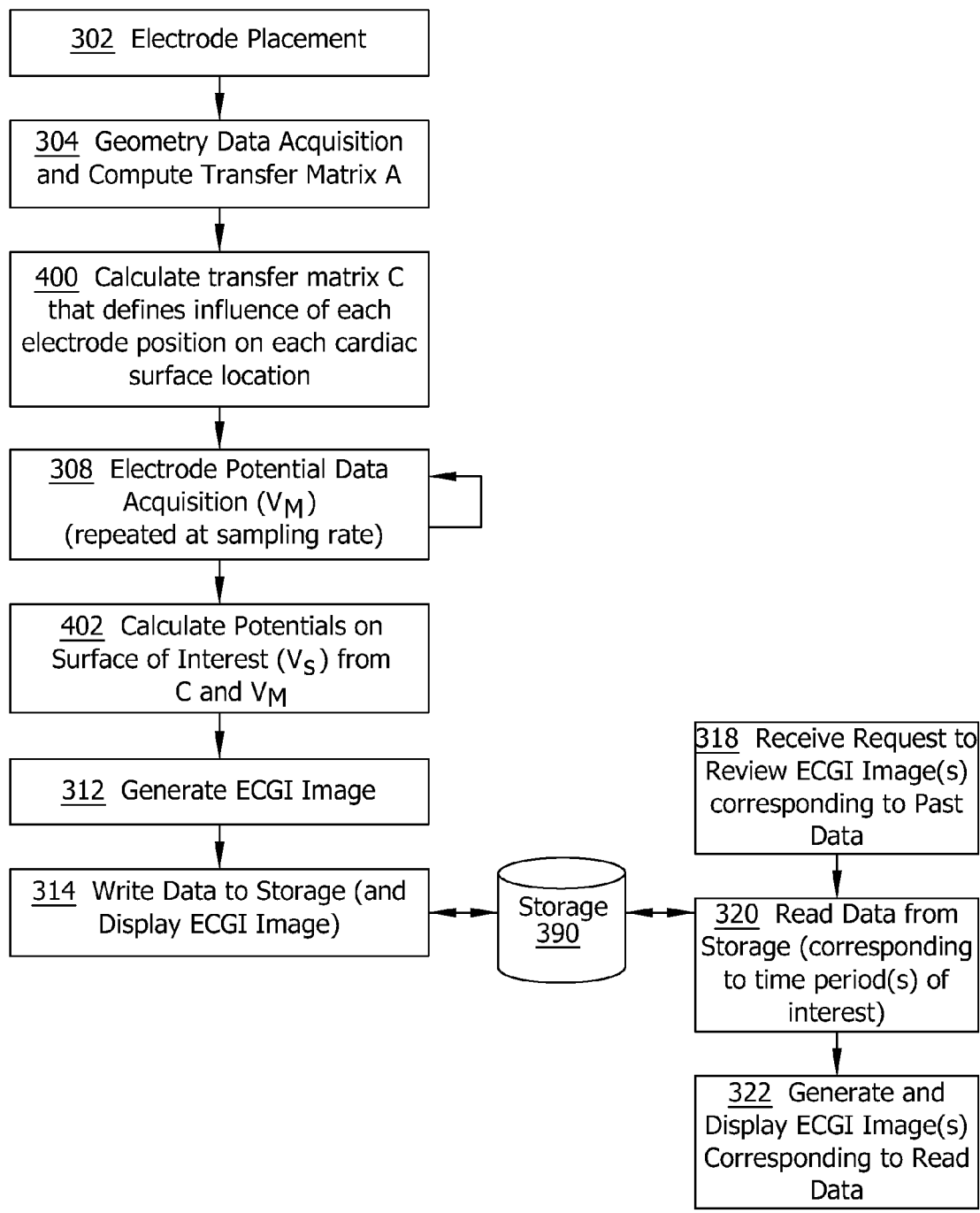

Real-Time ECGI:

FIGS. 4A and 4B illustrate exemplary process flows for practicing real-time ECGI. As noted above, with real-time ECGI, estimated electrical potentials on the surface of interest (and optionally corresponding ECGI images) can be computed with dramatically reduced latency to thereby allow an essentially "live" view of the surface of interest's electrical potentials.

With real-time ECGI, steps 302, 304, 308, 312, and 314 may operate as previously described. With the process flows of FIGS. 4A and 4B, it should be understood that step 308 is repeated at the sampling rate of the electrode measurement system (e.g., 1 kHz), and that steps 402, 312, and 314 may be performed for each sampled frame of $V_M$. Also, as shown in FIG. 4A, the process flow for real-time ECGI includes a step 400 wherein a transfer matrix C is calculated. Step 400 is performed prior to acquiring actual electrode potential measurements (step 308), optionally prior to the medical procedure or at the outset of the medical procedure.

The transfer matrix C defines a relative weight for how each electrode position influences the estimated electrical potentials for each location on the cardiac surface for which an electrical potential is to be estimated. As explained below, once C is known, the computation of $V_S$ from $V_M$ is a simple matter of matrix multiplication between C and $V_M$, thereby providing dramatic acceleration with respect to how quickly $V_S$ can be computed relative to previous techniques.

Figure 5A:
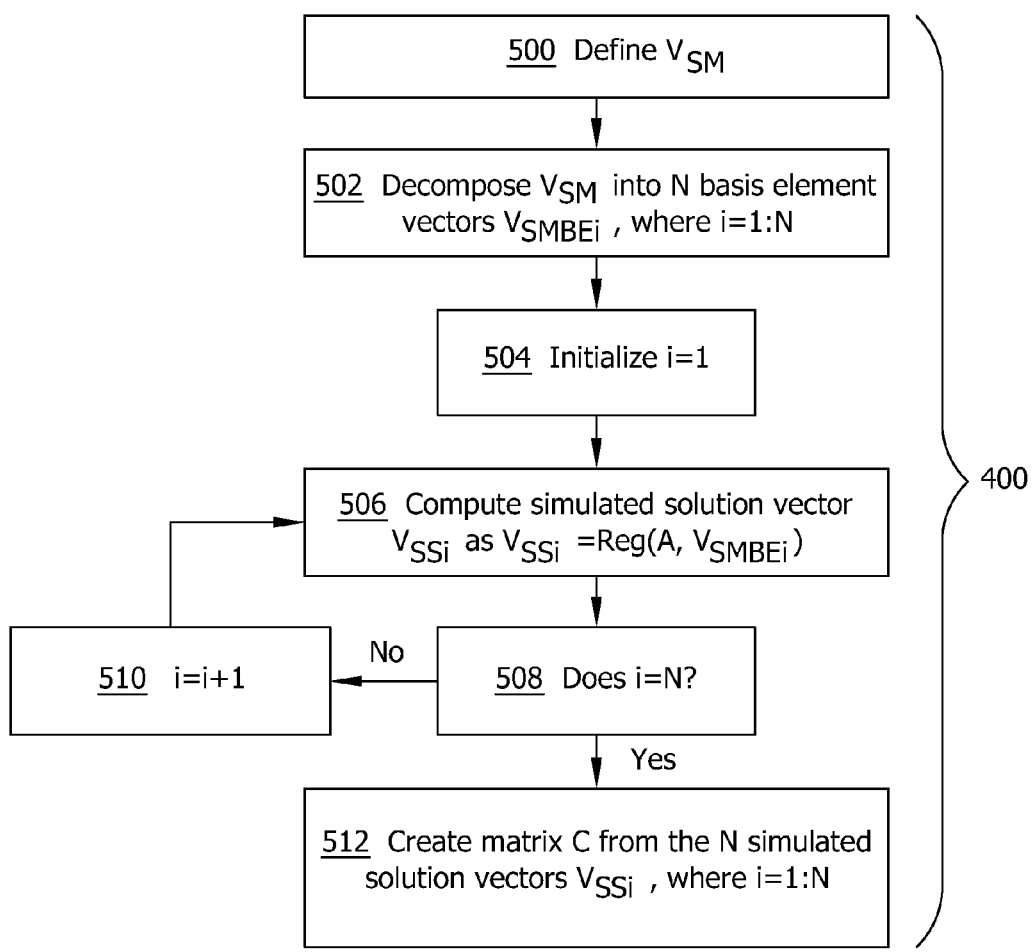

FIG. 5A depicts an exemplary process flow for step 400. At step 500, a simulated or "scout" measurement matrix $V_{SM}$ is defined. To define $V_{SM}$, one can assume that a simulated or "scout" $V_M$ vector exists wherein each element in the simulated $V_M$ vector is known.

Figure 5B:
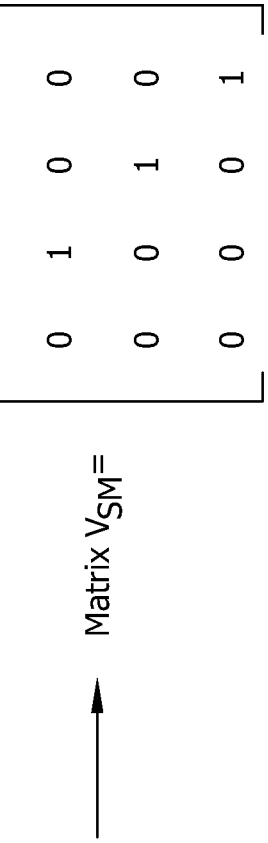

In one embodiment, this simulated $V_M$ assumes a value of "1" for all elements of the simulated $V_M$. However, as explained below, this need not be the case. An example of this where N equals 4 is shown in FIG. 5B. The matrix $V_{SM}$ can then be defined as an N×N matrix wherein the diagonal values for $V_{SM}$ are equal to the values of the simulated $V_M$ vector and all other matrix elements are zero. Thus, in the example of FIG. 5B, $V_{SM}$ is an 4×4 identity matrix.

At step 502, the matrix $V_{SM}$ is decomposed into a plurality N of basis element vectors $V_{SMBEi}$, for all values of i from 1 through N. To achieve this, each $V_{SMBEi}$ corresponds to column i of $V_{SM}$. An example of such decomposition is shown in FIG. 5C, wherein the 4×4 identity matrix $V_{SM}$ is decomposed into 4 basis element vectors $V_{SMBEi}$ through $V_{SMBE4}$.

At step 504, an iteration index i is initialized to 1. Then at step 506, the system computes a simulated solution vector $V_{SSi}$ as follows:

$$V_{SSi} = \text{Reg}(A, V_{SMBEi}) \qquad (5)$$

The regularization technique used to solve equation (5) is a linear regularization technique (such as Tikhonov regularization or a linear approximation of a nonlinear regularization technique (such as a linear approximation of the GMRes regularization technique)). Examples of additional linear regularization techniques that may optionally be used include Singular Value Decomposition (SVD) and Truncated Singular Value Decomposition (TSVD). As per steps 508 and 510, step 506 operates to compute $V_{SSi}$ according to equation (5) for all N values of i.

Each value of $V_{SSi}$ is a P element vector and represents the estimated cardiac surface potentials at all P cardiac surface locations if the $i^{th}$ electrode measured a "1" while all other electrodes measured a zero (or while all other electrodes are effectively "turned off").

Once all N values of $V_{SSi}$ have been calculated, step 512 operates to create the matrix C. To do so, each vector $V_{SSi}$ serves as the $i^{th}$ column in C. An example of creating matrix C in this manner is shown in FIG. 5D. Thus, as can be seen, C is a P×N matrix, and C represents how each electrode position relatively influences the estimated electrical potentials at each cardiac surface location for which the electrical potentials are to be estimated.

Once C has been calculated, the system can begin acquiring electrode measurements to define $V_M$ (step 308). Once $V_M$ is known, $V_S$ can readily be calculated at step 402 according to matrix multiplication as:

$$V_S = CV_M \qquad (6)$$

The computation according to Equation (6) is extremely fast because it is merely a matrix multiplication, which computers are well-suited to solve. Furthermore, due to the speed at which $V_S$ can be computed according to Equation (6), the process flow of FIG. 4A allows for "real-time" computations of $V_S$ from $V_M$ because the speed at which $V_S$ is computed according to Equation (6) is expected to greatly exceed the sampling rate used to measure $V_M$ (e.g., a $V_M$ sampling rate of around 1 kHz, or one frame of $V_M$ every millisecond). An illustration of this speed is described in connection with FIGS. 11A-11D.

The computation of $V_S$ from $V_M$ and C can be performed as a result of the following properties of the ECGI system. First, as per Equation (4):

$$V_S = \text{Reg}(A, V_M) \qquad (4)$$

Furthermore, as shown in FIG. 5C, when $V_{SM}$ is an N×N identity matrix:

$$V_M = \sum_{i=1}^{N} (V_M(i) * V_{SMBEi}) \qquad (7)$$

From the inherent properties of identity matrices, it also follows that:

$$V_M = V_{SM} * V_M \qquad (8)$$

Substituting the expression for $V_M$ in Equation (7) into Equation (4) thus yields:

$$V_S = \text{Reg}\left(A, \left(\sum_{i=1}^{N} (V_M(i) * V_{SMBEi})\right)\right) \qquad (9)$$

Given the linear properties of the linear regularization technique used for Reg( ), equation (9) can also be expressed as:

$$V_S = \sum_{i=1}^{N} (V_M(i) * \text{Reg}(A, V_{SMBEi})) \qquad (10)$$

As noted above in Equation (5), $V_{SSi}$ can be expressed as:

$$V_{SSi} = \text{Reg}(A, V_{SMBEi}) \qquad (5)$$

Substituting the expression for $V_{SSi}$ in Equation (5) into Equation (10) thus yields:

$$V_S = \sum_{i=1}^{N} (V_M(i) * V_{SSi}) \qquad (11)$$

Given that C is defined such that each column i of C is formed from vector $V_{SSi}$ (see FIG. 5D), and using the same algebraic properties that allow Equation (8) to be derived from Equation (7), this means that Equation (11) can also be expressed as Equation (6):

$$V_S = CV_M \qquad (6)$$

Figure 6B:
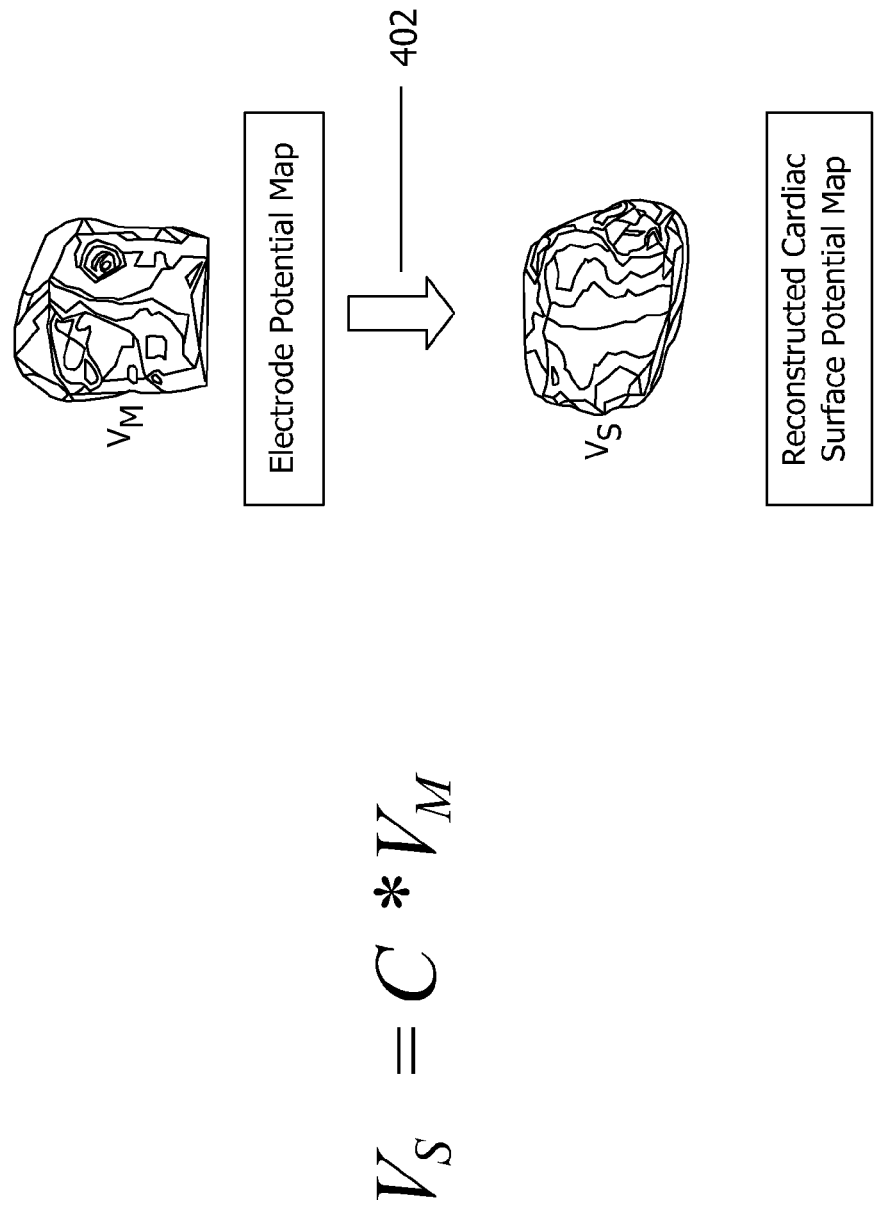

FIG. 6A illustrates a graphical depiction of how the process flow of FIG. 5A can progress from step 502 to step 512. FIG. 6A depicts examples of how the $1^{st}$ and $N^{th}$ electrodes, when simulating a measurement of "1" while all other electrodes simulate a measurement of zero, would influence the estimation of cardiac surface electrical potentials at all P cardiac surface locations. FIG. 6B provides a graphical illustration of how the process flow of FIG. 4A progresses from step 308 to step 402 according to Equation (6).

Figure 4C:
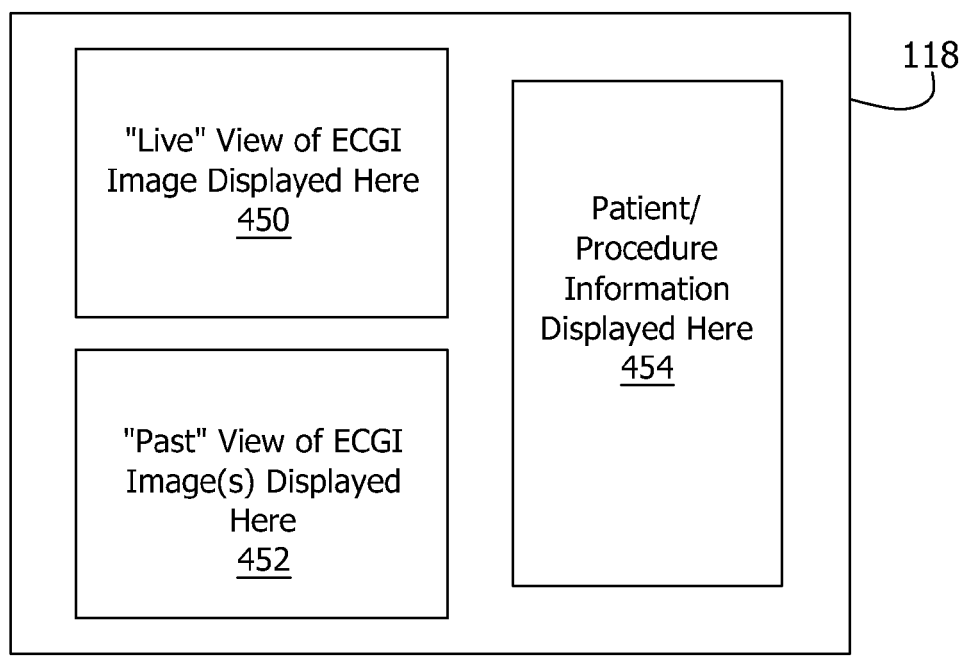
FIG. 4C depicts an exemplary monitor that can display ECGI images in accordance with the embodiment of FIG. 4B.

FIG. 4B illustrates a process flow that largely corresponds to the process flow of FIG. 3B but for a "real-time" embodiment of ECGI. As such, steps 302, 304, 400, 308, 402, 314, 318, 320, and 322 operate as previously described. Through the process flow of FIG. 4B, a practitioner may not only generate a "live" view of the ECGI data computed at step 402, but can also generate a "past" view of ECGI data computed during a previous iteration of step 402. Such a simultaneous display of a "live" view and a "past" view corresponding to a time frame of interest may provide certain insights to a practitioner about a patient's heart condition. FIG. 4C depicts an exemplary output device 118 (such as a display monitor) wherein a section 450 of the monitor is used to display a "live" view of ECGI data and where another section 452 of the monitor is used to display the desired "past" view of ECGI data. Yet another section 454 may optionally be set aside to display miscellaneous information such a patient or procedure data.

FIGS. 11A-11D depicts exemplary results for practicing "real-time" ECGI such as can be produced via the process flow of FIG. 4A. In the example of FIGS. 11A-11D, 242 body surface electrodes were used to measure $V_M$, and $V_S$ was estimated for 502 epicardial sites. Thus, in this example, N was 242 and P was 502. Such values for N and P can be characterized as typical for clinical applications of ECGI. FIGS. 11A-11D depict a comparison of using (1) "non real-time" ECGI techniques such as that described in connection with the on-site embodiments of FIGS. 3A and 3B or the "off-site" techniques described in the above-referenced and incorporated patents and patent applications, and (2) the "real-time" techniques described in connection with FIG. 4A. The same data set was used for the electrode data for both the "non-real-time" and "real-time" ECGI techniques. Also, BEM meshing was used to define the geometry data for transfer matrix A with respect to both the "non-real-time" and "real-time" ECGI techniques. Further still, in this particular example, the "non-real-time" ECGI technique used to generate the estimated epicardial potentials was the technique described in connection with the above-referenced and incorporated U.S. Pat. No. 6,772,004.

Figure 11A:
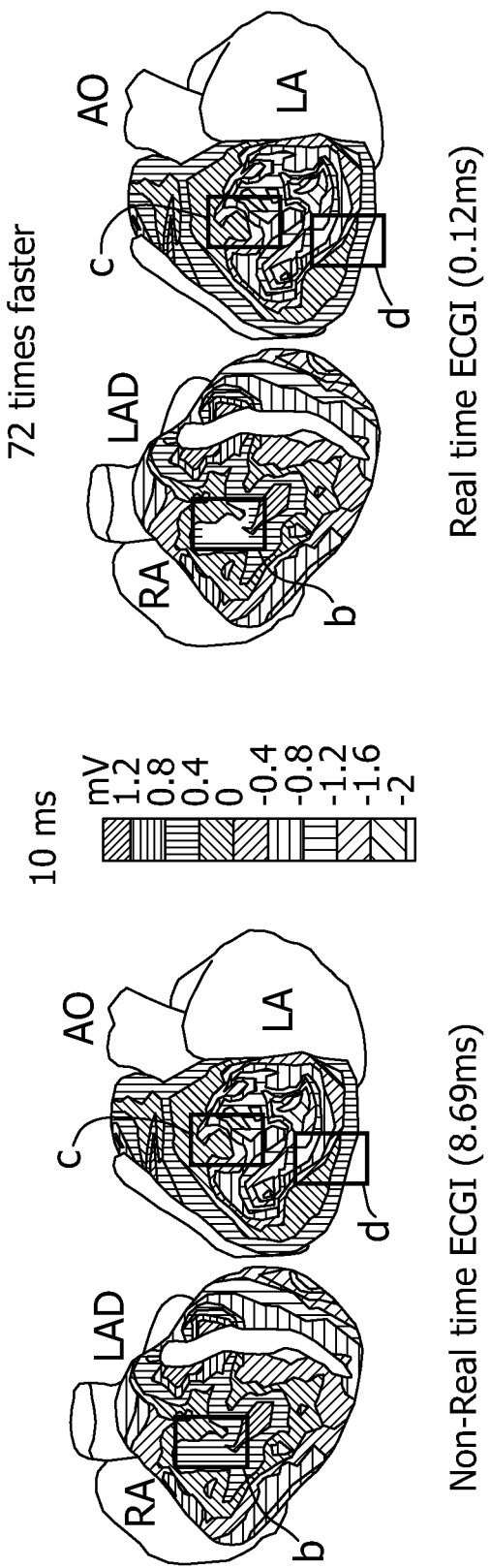
FIGS. 11A-11D depict a comparison of results that can be produced using "real-time" ECGI versus "offline" ECGI.
Figure 11B:
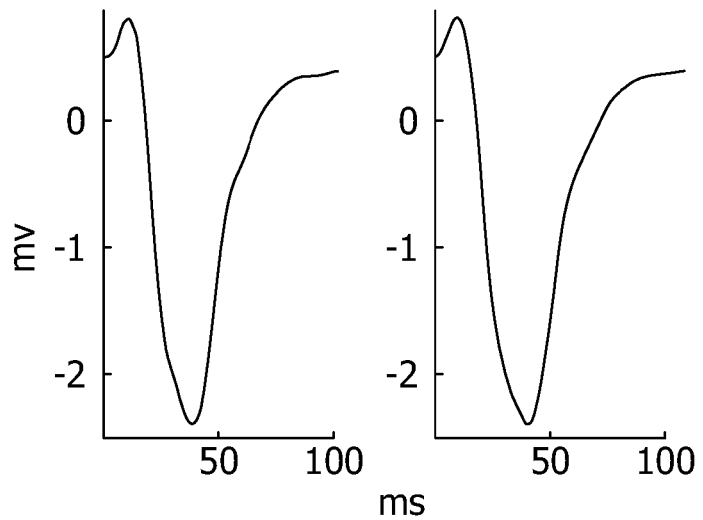
Figure 11C:
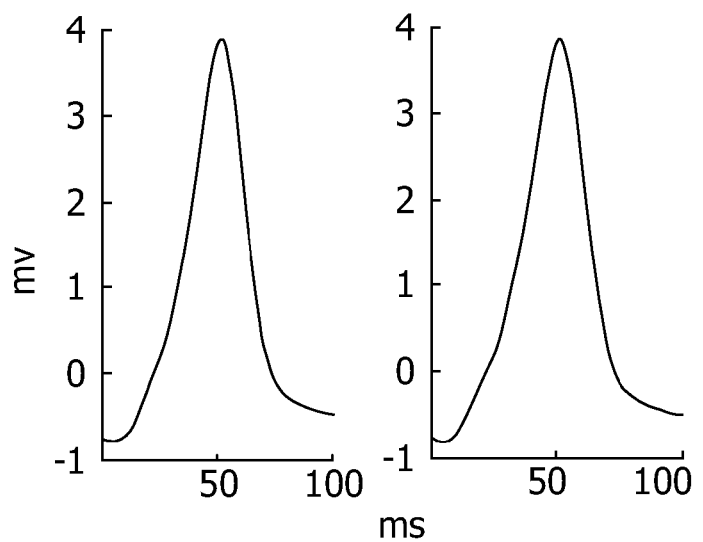
Figure 11D:
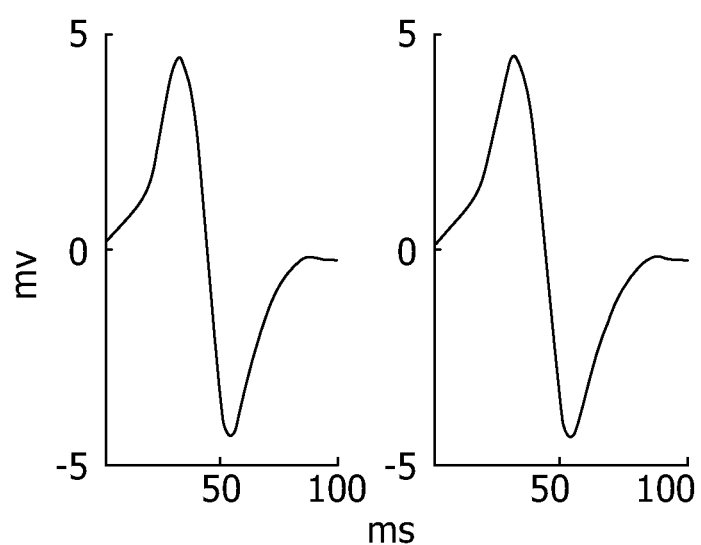

The reconstructed map of epicardial electrical potential estimates shown on the left of FIG. 11A depicts the epicardial electrical potential estimates estimated using an "non-real-time" ECGI technique. The reconstructed map of epicardial electrical potential estimates shown on the right of FIG. 11A depicts the epicardial electrical potential estimates estimated using the "real-time" ECGI technique described in connection with FIG. 4A. The plots of FIG. 11B depict electrograms reconstructed at location "b" on the epicardium (see the maps) for both the "non-real-time" and "real-time" ECGI techniques. The plots of FIG. 11C depict electrograms reconstructed at location "c" on the epicardium (see the maps) for both the "non-real-time" and "real-time" ECGI techniques. The plots of FIG. 11D depict electrograms reconstructed at location "d" on the epicardium (see the maps) for both the "non-real-time" and "real-time" ECGI techniques. As can be seen, from the maps of FIG. 11A and the plots of FIGS. 11B, 11C, and 11D, the results generated from non-real-time and real-time ECGI are identical. However, as noted in FIG. 11A, the "real-time" ECGI technique produced the $V_S$ data approximately 72 times faster than the "non-real-time" ECGI technique (0.12 ms versus 8.69 ms). These measures represent how long it took to perform step 310 for non-real-time ECGI and step 402 for the real-time ECGI. It should be understood that step 310 will be the same for both the "on-site" ECGI embodiment described herein and the offline techniques such as those described in the above-referenced and incorporated U.S. Pat. No. 6,772,004. Given the dramatic improvement in computing $V_S$ from $V_M$ for the "real-time" technique according to step 402 relative to step 310, the inventors believe that the "real-time" ECGI technique described herein represents a pioneering breakthrough toward the goal of deploying ECGI as a valuable guiding or interventional tool during medical procedures such as catheter ablation of arrhythmias, cardiac resynchronization therapy for heart failures, etc.

It should be noted that, while an exemplary embodiment of the "real-time" ECGI uses a simulated $V_M$ where all "1"s are used as the simulated measurements (thus resulting in $V_{SM}$ being an identity matrix), a practitioner could optionally use any arbitrary number for the simulated $V_M$ values. For example, it could be assumed that each electrode will measure a value of 3.623, in which case $V_{SM}$ would be an N×N matrix with a value of 3.623 for all diagonal elements and a value of zero for all non-diagonal elements. In such an exemplary embodiment, Equation (6) would simply be modified to: $V_S=C^*(1/3.623)V_M$ Further still, it should be understood that the different simulated values on the diagonal of $V_{SM}$ can have different values relative to each other so long as those values are known in advance to allow that they later be scaled out during the computation of $V_S$.

It should also be noted that the process flows of FIGS. 4A and 4B may optionally employ start and stop steps 306 and 316 as described in connection with the process flows of FIGS. 3A and 3B.

With respect to the embodiments described herein, the inventors note that the resultant ECGI images can be stored in computer memory, and that a practitioner may step through the generated images in "slow motion" or pause on a single image. Thus, the exemplary embodiments of ECGI disclosed herein allow medical personnel to view a particular time period of interest with a very high degree of image resolution and clarity.

The inventors also note that the "on-site" and "real-time" techniques described herein may be applied with effectiveness to both meshed and meshless ECGI techniques. For purposes of clarity, the inventors will now describe how "on-site" and "real-time" ECGI can be practiced with respect to a meshless ECGI technique such as that described in PCT Publication WO 2007/013994.

Figure 7:
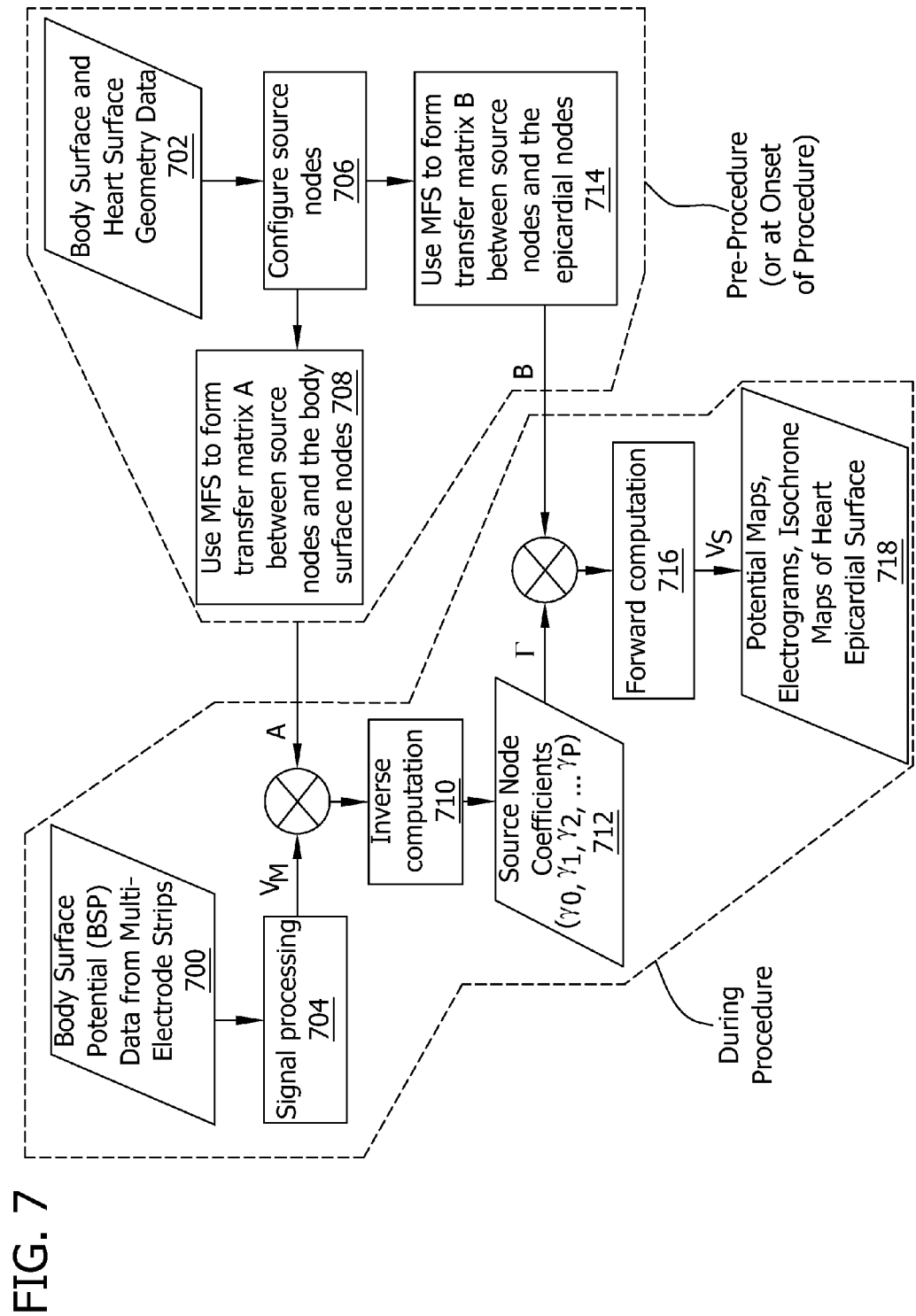
FIG. 7 depicts an exemplary process flow for an on-site embodiment of meshless ECGI.

Exemplary Meshless on-Site ECGI Embodiment:

FIG. 7 depicts an example where the process flow of FIGS. 3A and 3B can be implemented in a meshless ECGI environment. FIG. 7 depicts a process flow for meshless ECGI, as described in connection with PCT Publication WO 2007/013994. To perform such meshless ECGI in an on-site manner, steps 702, 706, 708, and 714 are performed before acquiring electrode potential measurements, and optionally prior to the medical procedure or at the outset of the medical procedure, while steps 700, 704, 710, 712, 716, and 718 are performed during the medical procedure. Additional details regarding steps 700, 702, 704, 706, 708, 710, 712, 714, 716, and 718 can be found in PCT Publication WO 2007/013994.

Figure 8:
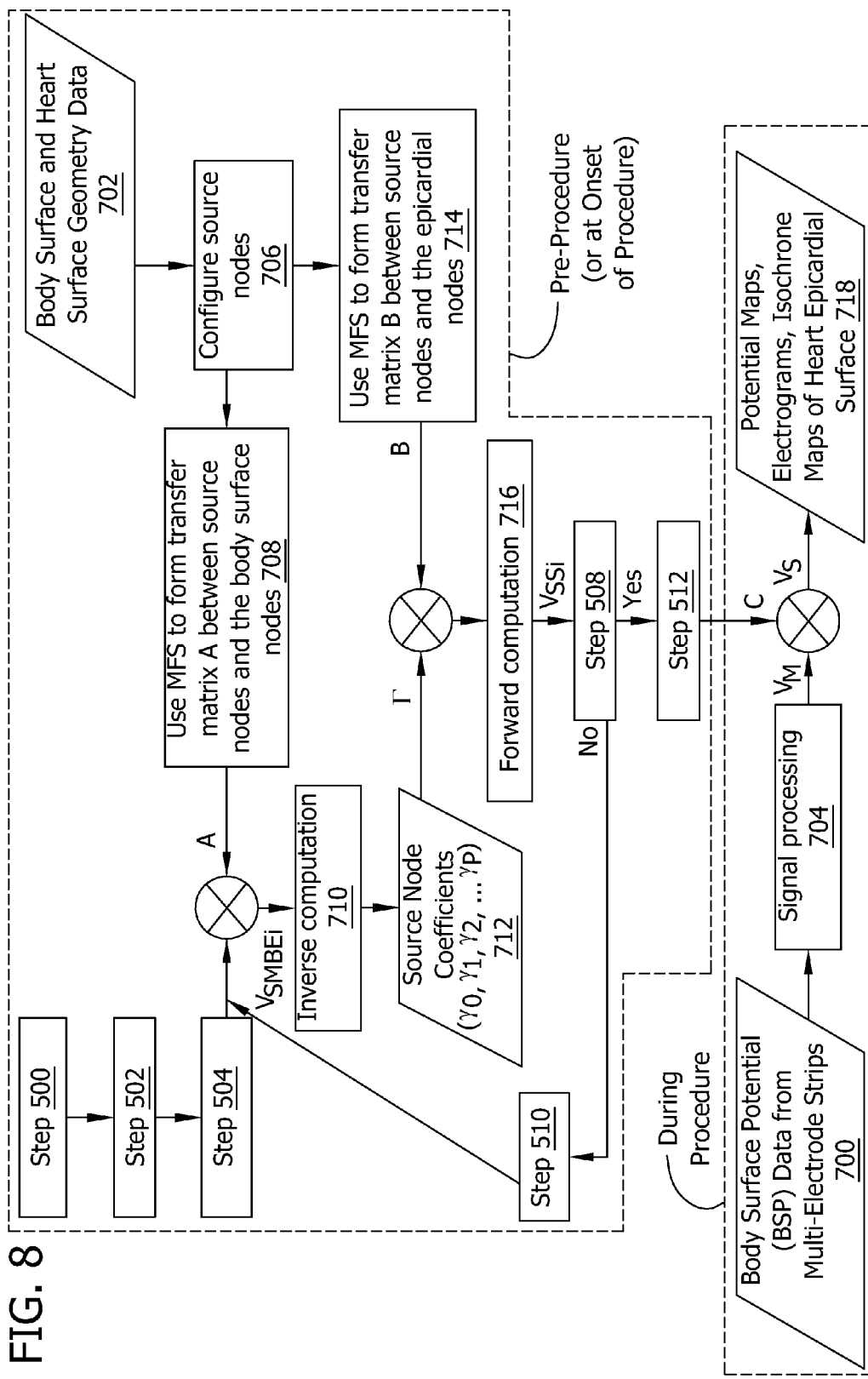
FIG. 8 depicts an exemplary process flow for a real-time embodiment of meshless ECGI.

Exemplary Meshless Real-Time ECGI Embodiment:

FIG. 8 depicts an example where the process flow of FIGS. 4A and 4B can be implemented in a meshless ECGI environment. To perform such meshless ECGI in real-time manner. As noted above, additional details regarding steps 700, 702, 704, 706, 708, 710, 712, 714, 716, and 718 can be found in PCT Publication WO 2007/013994.

Figure 9:
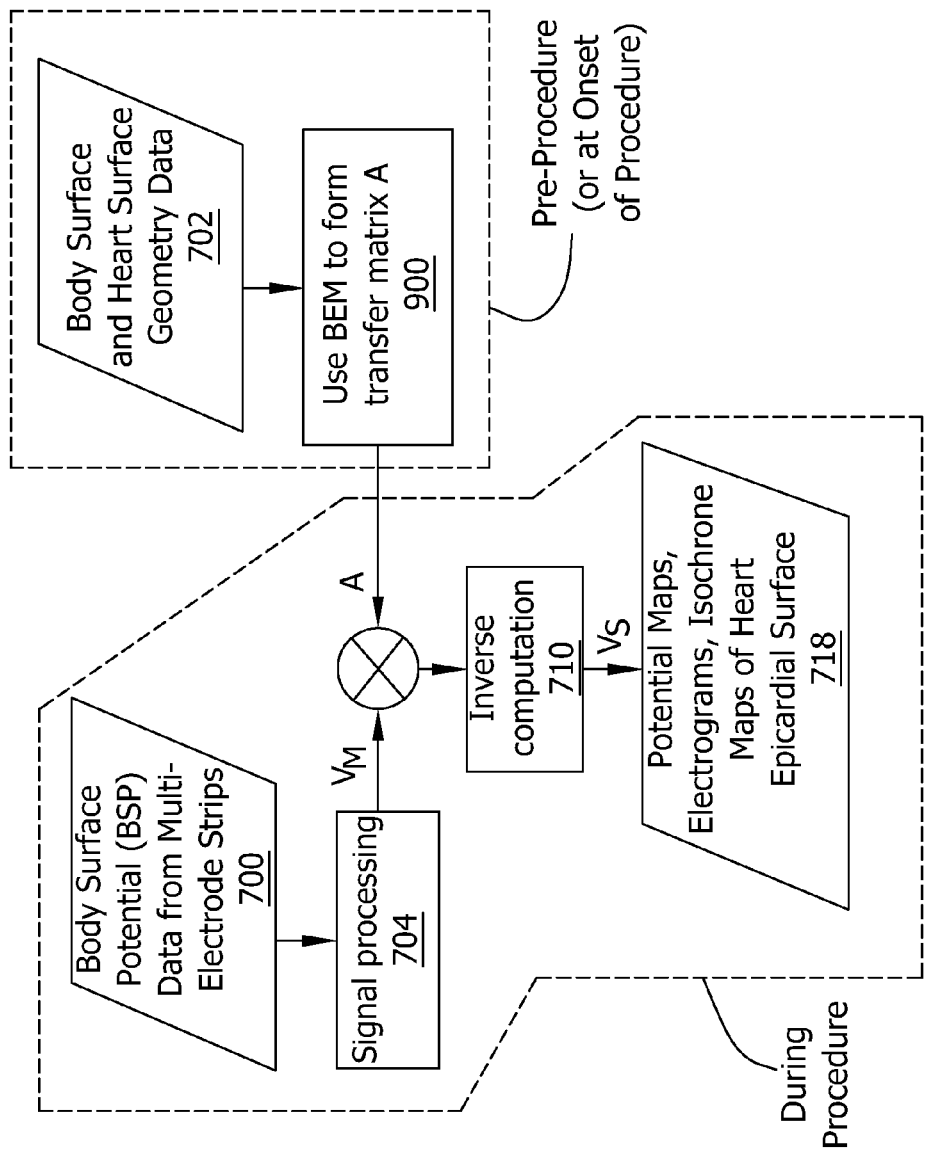
FIG. 9 depicts an exemplary process flow for an on-site embodiment of meshed ECGI.

Exemplary Meshed on-Site ECGI Embodiment:

FIG. 9 depicts an example where the process flow of FIGS. 3A and 3B can be implemented in a meshed ECGI environment. With this embodiment, relative to the process flow of FIG. 7, it can be seen that the transfer matrix B need not be computed (and the corresponding downstream computations based on B as well as step 706 can be eliminated), and step 708 is replaced with a step 900 that uses the Boundary Element Method (BEM) to form transfer matrix A, as described in connection with the above-referenced and incorporated U.S. Pat. No. 6,772,004.

Figure 10:
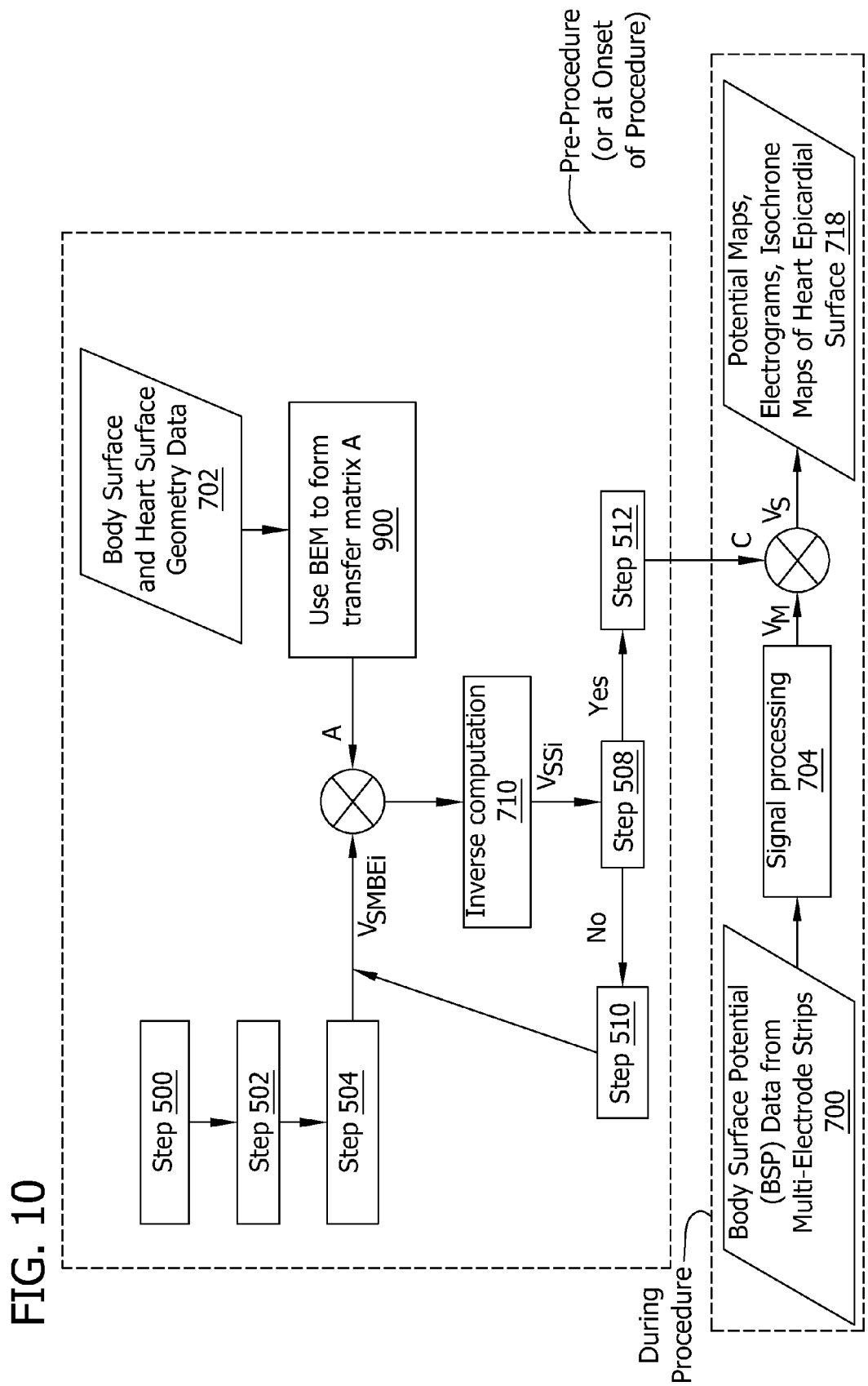
FIG. 10 depicts an exemplary process flow for a real-time embodiment of meshed ECGI.

Exemplary Meshed Real-Time ECGI Embodiment:

FIG. 10 depicts an example where the process flow of FIGS. 4A and 4B can be implemented in a meshed ECGI environment. FIG. 10 largely corresponds to FIG. 8, albeit without the computation of transfer matrix B (and its related downstream operations as well as step 706) and with the inclusion of step 900.

Exemplary Operating Environment

Methods described herein may be performed by a computer or computing device. A computer or computing device includes one or more processors or processing units, each containing one or more processing cores, system memory, and some form of computer readable media. One or more processors or processing units may be programmed with instructions that cause the processors or processing units to perform one or more of the methods described herein. In some embodiments, a processor is programmed by providing executable instructions on a computer readable medium or media. By way of example and not limitation, computer readable media comprise computer storage media and communication media. Computer storage media include volatile and nonvolatile, removable and non-removable media implemented in any method or technology for storage of information such as computer readable instructions, data structures, program modules, executable components, or other data. Communication media typically embody computer readable instructions, data structures, program modules, or other data in a modulated data signal such as a carrier wave or other transport mechanism and include any information delivery media. Combinations of any of the above are also included within the scope of computer readable media.

Although described in connection with an exemplary computing system environment, embodiments of the invention are operational with numerous other general purpose or special purpose computing system environments or configurations. The computing system environment is not intended to suggest any limitation as to the scope of use or functionality of any aspect of the invention.

Embodiments of the invention may be described in the general context of computer-executable instructions, such as program modules, executed by one or more computers or other devices. The computer-executable instructions may be organized into one or more computer-executable components or modules. Generally, program modules include, but are not limited to, routines, programs, objects, components, and data structures that perform particular tasks or implement particular abstract data types. Aspects of the invention may be implemented with any number and organization of such components or modules. For example, aspects of the invention are not limited to the specific computer-executable instructions or the specific components or modules illustrated in the figures and described herein. Other embodiments of the invention may include different computer-executable instructions or components having more or less functionality than illustrated and described herein.

In an exemplary embodiment, one or more computer-readable media includes computer-executable components. The components include a transfer matrix computation component, a measurement component, and an estimation component. The transfer matrix computation component, when executed by at least one processor, causes the at least one processor to compute a transfer matrix. The measurement component, when executed by the at least one processor, causes the at least one processor to measure a plurality of electrical potentials. The estimation component, when executed by the at least one processor, causes the at least one processor to compute an estimation of electrical potentials on a surface of interest based at least in part on the measured electrical potentials and the computed transfer matrix. The at least one processor computes the transfer matrix before the at least one processor measures the plurality of electrical potentials.

While the making and use of various embodiments of the invention are discussed in detail above, the embodiments of the invention provide many applicable inventive concepts that may be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the embodiments of the invention. Terms such as "a," "an" and "the" are not intended to refer to only a singular entity, but include the general class of which a specific example may be used for illustration. The terminology herein is used to describe specific embodiments of the invention, but their usage does not delimit the invention, except as outlined in the claims.

The order of execution or performance of the operations in embodiments of the invention illustrated and described herein is not essential, unless otherwise specified. For example, it is contemplated that executing or performing a particular operation before, contemporaneously with, or after another operation is within the scope of aspects of the invention. Embodiments of the invention may include additional or fewer operations than those disclosed herein.

What is claimed is:

1. A method comprising:

computing, by a computer comprising a processor, a transfer matrix representing a relative influence that each of the respective electrode locations for the measured electrical potentials has on the estimation of electrical potentials for the locations on the surface of interest prior to measuring the plurality of electrical potentials;

measuring the plurality of electrical potentials via the plurality of electrodes at respective electrode locations on a patient's body;

receiving, by the computer, data corresponding to the plurality of electrical potentials measured via the plurality of electrodes at respective electrode locations; and computing, by the computer, an estimation of electrical potentials for locations on a surface of interest based at least in part on the measured plurality of electrical potentials and the computed transfer matrix, wherein the locations on the surface of interest are different from the electrode locations; and displaying an image of the surface of interest including the estimated electrical potentials for locations on the surface of interest.

2. The method of claim 1, wherein the surface of interest comprises a cardiac surface.

3. The method of claim 2, wherein computing the transfer matrix occurs prior to a medical procedure or at an outset of the medical procedure, and wherein said receiving data corresponding to the plurality of electrical potentials and said computing the estimation occur during the medical procedure.

4. The method of claim 3, wherein said receiving data corresponding to the plurality of electrical potentials and said computing the estimation occur on-site with respect to where the medical procedure is being performed.

5. The method of claim 2, wherein the cardiac surface comprises at least one selected from the group consisting of an epicardial surface and an endocardial surface.

6. The method of claim 2, wherein the estimation is computed via a meshless electrocardiographic imaging (ECGI) procedure.

7. The method of claim 2, further comprising using the computed estimation to evaluate a result of the medical procedure.

8. The method of claim 1, wherein computing the transfer matrix comprises computing by the processor a first transfer matrix and a second transfer matrix, both transfer matrices being computed prior to said measuring via the plurality of electrodes, the first transfer matrix representing a geometrical relationship between each electrode location of the plurality electrodes where the measured electrical potentials are measured and a plurality of locations on the surface of interest for which the estimated electrical potentials are estimated, the second transfer matrix representing a relative influence that each of the plurality of electrode locations for the measured electrical potentials has on the estimated potentials for the locations on the surface of interest, and wherein computing the estimation comprises multiplying the second transfer matrix and the measured electrical potentials.

9. The method of claim 8, wherein computing the estimation comprises computing the estimation in real-time with respect to said receiving data corresponding to the measured electrical potentials.

10. The method of claim 8, further comprising:
defining a simulated measurement of the measured electrical potentials;
computing a plurality of simulated estimations of electrical potentials on the surface of interest based on the simulated measurement and the first transfer matrix; and
creating the second transfer matrix from the plurality of simulated estimations.

11. The method of claim 10, wherein said computing the plurality of simulated estimations comprises computing the plurality of simulated estimations of electrical potentials using a linear regularization technique.

12. A system comprising:
a signal acquisition device comprising a plurality of electrical inputs to receive a plurality of electrical potential measurements from electrodes to be arranged at respective locations on a patient's body to measure the plurality of respective electrode locations; and
a processing device comprising a processor programmed to:
compute a transfer matrix representing a relative influence that each of the respective electrode locations for the measured electrical potentials has on the estimation of electrical potentials for the locations on the surface of interest prior to measuring the plurality of electrical potential measurements;
receive the plurality of electrical potential measurements from the signal acquisition device; and
compute an estimation of electrical potentials on a cardiac surface of interest based at least in part on the plurality of electrical potential measurements and the computed transfer matrix, wherein the processor is programmed to perform the transfer matrix computation in the absence of the electrical potential measurements, wherein the locations on the surface of interest are different from the electrode locations; and
a display to display an image of the cardiac surface of interest and either the estimation of the electrical potentials for the locations on the cardiac surface of interest or information derived from the estimation of the electrical potentials for locations on the cardiac surface of interest.

13. The system of claim 12, wherein the processor is further programmed to compute the estimation via a meshless ECGI technique.

14. The system of claim 12, wherein the processor is further programmed to compute a plurality of transfer matrices, the plurality of transfer matrices comprising a first transfer matrix and a second transfer matrix, wherein the processor is further programmed to compute both transfer matrices prior to receiving the electrical potential measurements, the first transfer matrix representing a geometrical relationship between each electrode location of the plurality electrodes where the measured electrical potentials are measured and a plurality of locations on the surface of interest for which the estimated electrical potentials are estimated, the second transfer matrix representing a relative influence that each of the plurality of electrode locations for the measured electrical potentials has on the estimated potentials for the locations on the surface of interest, and wherein the processor is further programmed to compute the estimation by multiplying the first transfer matrix and the electrical potential measurements.

15. The system of claim 14, wherein the processor is further programmed to:
generate an image for display based on the computed estimation; and
perform the estimation computation and the image generation in real-time with respect to receiving the electrical potential measurements.

16. The system of claim 14, wherein the processor is further programmed to:
define a simulated measurement of the electrical potential measurements;
compute a plurality of simulated estimations of electrical potentials on the surface of interest based on the simulated measurement and the first transfer matrix; and
create the second transfer matrix from the plurality of simulated estimations.

17. The system of claim 16, wherein the processor is further programmed to compute the plurality of simulated estimations using a linear regularization technique.

* * * * *